(12) United States Patent
Komatsubara

(10) Patent No.: US 9,888,671 B2
(45) Date of Patent: Feb. 13, 2018

(54) DISPOSABLE DIAPER FOR PETS

(71) Applicant: UNI-CHARM CORPORATION, Ehime (JP)

(72) Inventor: Daisuke Komatsubara, Kanonji (JP)

(73) Assignee: UNI-CHARM CORPORATION, Ehime (JP)

( * ) Notice: Subject to any disclaimer, the term of this patent is extended or adjusted under 35 U.S.C. 154(b) by 0 days.

(21) Appl. No.: 14/651,230

(22) PCT Filed: Nov. 15, 2013

(86) PCT No.: PCT/JP2013/080951
§ 371 (c)(1),
(2) Date: Jun. 11, 2015

(87) PCT Pub. No.: WO2014/091871
PCT Pub. Date: Jun. 19, 2014

(65) Prior Publication Data
US 2015/0305308 A1    Oct. 29, 2015

(30) Foreign Application Priority Data
Dec. 13, 2012    (JP) .................................. 2012-272362

(51) Int. Cl.
*A01K 23/00*    (2006.01)
*A61F 13/15*    (2006.01)

(52) U.S. Cl.
CPC .... *A01K 23/00* (2013.01); *A61F 2013/15186* (2013.01)

(58) Field of Classification Search
CPC .................................................... A01K 23/00
(Continued)

(56) References Cited

U.S. PATENT DOCUMENTS

| 4,917,683 A | 4/1990 | Thompson |
| 5,234,421 A | 8/1993 | Lowman |

(Continued)

FOREIGN PATENT DOCUMENTS

| CN | 2281647 Y | 5/1998 |
| CN | 200987318 Y | 12/2007 |

(Continued)

OTHER PUBLICATIONS

International Search Report dated Feb. 10, 2014 in International Application No. PCT/JP2013/080951.

(Continued)

*Primary Examiner* — Monica L Williams
*Assistant Examiner* — Aaron M Rodziwicz
(74) *Attorney, Agent, or Firm* — Hauptman Ham, LLP

(57) ABSTRACT

A disposable diaper for pets having a shortest straight line point being further on a stomach-side waist area side than a diaper center point, and comprising: a rear-side waist area; a stomach-side waist area; a crotch area; a flap section provided in the stomach-side waist area and having an end section in the rear-side direction; a diaper longitudinal direction center line; the diaper center point; a tail insertion opening; an absorbent core; an attachment section arranged in the flap section; an attachment section intermediate point; an attachment area that receives the attachment section; and the shortest straight line point being a point on the diaper longitudinal direction center line at the shortest direct distance, via a rear-side end section of the flap section in a straight line from the attachment section center point to the diaper longitudinal direction center line.

17 Claims, 22 Drawing Sheets

(58) Field of Classification Search
USPC .......................................... 119/897, 868, 869
See application file for complete search history.

(56) References Cited

U.S. PATENT DOCUMENTS

| | | | |
|---|---|---|---|
| 5,555,847 | A | 9/1996 | Kelly |
| 5,954,015 | A * | 9/1999 | Ohta .................. A01K 23/00 119/850 |
| 6,142,105 | A * | 11/2000 | McKnight .............. A01K 23/00 119/850 |
| 8,020,523 | B2 | 9/2011 | Ikegami et al. |
| 9,265,234 | B2 | 2/2016 | Komatsubara et al. |
| 9,332,731 | B2 | 5/2016 | Komatsubara et al. |
| 2005/0154367 | A1 | 7/2005 | Ikegami |
| 2006/0217678 | A1* | 9/2006 | Ikegami .................. A01K 23/00 604/386 |
| 2007/0142798 | A1 | 6/2007 | Goodlander et al. |
| 2007/0149941 | A1* | 6/2007 | Ikegami .................. A01K 23/00 604/385.09 |
| 2009/0247980 | A1 | 10/2009 | Aiken |
| 2010/0229803 | A1* | 9/2010 | Meissner ............... A01K 23/00 119/868 |
| 2011/0192357 | A1* | 8/2011 | Pellegrini .............. A01K 23/00 119/850 |
| 2011/0209675 | A1 | 9/2011 | Esperon |
| 2012/0226252 | A1 | 9/2012 | Yago et al. |
| 2012/0245550 | A1 | 9/2012 | Sakaguchi et al. |
| 2014/0076246 | A1 | 3/2014 | Komatsubara et al. |
| 2015/0196009 | A1 | 7/2015 | Komatsubara et al. |
| 2015/0272713 | A1 | 10/2015 | Komatsubara |
| 2015/0327517 | A1 | 11/2015 | Komatsubara |
| 2016/0008183 | A1 | 1/2016 | Komatsubara |

FOREIGN PATENT DOCUMENTS

| | | | |
|---|---|---|---|
| CN | 102573738 | A | 7/2012 |
| EP | 0692188 | A1 | 1/1996 |
| EP | 1535509 | A1 * | 6/2005 ............. A01K 23/00 |
| EP | 1709870 | A1 | 10/2006 |
| JP | 10075679 | A * | 3/1998 |
| JP | 11000073 | A * | 1/1999 |
| JP | 2003102313 | A * | 4/2003 |
| JP | 2003210062 | A * | 7/2003 |
| JP | 2003220090 | A * | 8/2003 |
| JP | 2003245024 | A * | 9/2003 |
| JP | 2004-159591 | A | 6/2004 |
| JP | 2004159591 | A * | 6/2004 |
| JP | 3625203 | B2 | 3/2005 |
| JP | 3112749 | U | 8/2005 |
| JP | 2006-34872 | A | 2/2006 |
| JP | 2006-271212 | A | 10/2006 |
| JP | 2006-281545 | A | 10/2006 |
| JP | 2007-159420 | A | 6/2007 |
| JP | 2007135412 | A * | 6/2007 |
| JP | 2007228884 | A * | 9/2007 |
| JP | 2008193920 | A | 8/2008 |
| JP | 4445422 | B2 | 4/2010 |
| JP | 4467512 | B2 | 5/2010 |
| JP | 2012110299 | A * | 6/2012 |
| JP | 2012139128 | A * | 7/2012 |
| JP | 2012183045 | A * | 9/2012 |
| JP | 2012-200206 | A | 10/2012 |
| WO | WO 2012132886 | A1 | 10/2012 |

OTHER PUBLICATIONS

Office Action in CN Application No. 201380065183.9, dated Jan. 18, 2017.
Office Action in CN Application No. 201380065627.9, dated Jan. 24, 2017.
Office Action in CN Application No. 201380065637.2, dated Jan. 10, 2017.
Office Action in CN Application No. 201380065333.6, dated Jan. 22, 2017.
Extended European Search Report corresponding to EP13862081.0, dated Jun. 16, 2016.
Extended European Search Report in EP Application No. 13861809.5, dated Jul. 20, 2016.
Extended European Search Report in EP Application No. 13861991.1, dated Jul. 15, 2016.
Extended European Search Report in EP Application No. 13862127.1, dated Jul. 28, 2016.
Extended European Search Report in EP Application No. 13862288.1, dated Jul. 15, 2016.
Extended European Search Report in EP Application No. 13863278.1, dated Jul. 15, 2016.
International Preliminary Report on Patentability in PCT/JP2013/082890, dated Jun. 16, 2015.
International Search Report in PCT/JP2013/080346, dated Feb. 10, 2014.
International Search Report dated Feb. 10, 2014 in International Application No. PCT/JP2013/080347.
International Search Report dated Feb. 10, 2014 in International Application No. PCT/JP2013/080348.
International Search Report dated Feb. 10, 2014 in International Application No. PCT/JP2013/080953.
International Search Report dated Feb. 10, 2014 in International Application No. PCT/JP2013/081453.
International Search Report dated Feb. 10, 2014 in International Application No. PCT/JP2013/081454.
International Search Report dated Feb. 10, 2014 in International Application No. PCT/JP2013/081455.
International Search Report dated Feb. 10, 2014 in International Application No. PCT/JP2013/082890.
International Search Report dated Feb. 18, 2014 in International Application No. PCT/JP2013/082891.
Office Action (2nd) in CN Application No. CN201380065617.5, dated Oct. 21, 2016.
Office Action in CN Application No. 201380065150.4, dated Apr. 19, 2016.
Office Action in CN Application No. 201380065183.9, dated May 26, 2016.
Office Action in CN Application No. 201380065247.5, dated Apr. 25, 2016.
Office Action in CN Application No. 201380065333.6, dated May 23, 2016.
Office Action in CN Application No. 201380065354.8, dated Mar. 7, 2016.
Office Action in CN Application No. 201380065617.5, dated Feb. 29, 2016.
Office Action in CN Application No. 201380065627.9, dated May 6, 2016.
Office Action in CN Patent Application No. 201380065672.4, dated Feb. 29, 2016.
Office Action in JP Application No. 2012-272355, dated Jun. 8, 2016.
Office Action in JP Application No. 2012-272366, dated Aug. 25, 2015.
Office Action in JP Application No. 2012-272371, dated Jun. 10, 2016.
Office Action in JP Application No. 2012-272379, dated Jun. 10, 2016.
Office Action in JP Application No. 2012-272383, dated Jun. 10, 2016.
Office Action in U.S. Appl. No. 14/651,227, dated Dec. 13, 2016.
Office Action in U.S. Appl. No. 14/651,228, dated Nov. 18, 2016.
Office Action in U.S. Appl. No. 14/651,229, dated Nov. 21, 2016.
Office Action in U.S. Appl. No. 14/651,231, dated Nov. 1, 2016.
Office Action in U.S. Appl. No. 14/651,648, dated Nov. 2, 2016.
Office Action in U.S. Appl. No. 14/651,667, dated Dec. 13, 2016.
Office Action in U.S. Appl. No. 14/651,668, dated Nov. 25, 2016.
Written Opinion in International Application No. PCT/JP2013/080346, dated Feb. 10, 2014.
Written Opinion in International Application No. PCT/JP2013/080348, dated Feb. 10, 2014.

(56) References Cited

OTHER PUBLICATIONS

Written Opinion in International Application No. PCT/JP2013/080953, dated Feb. 10, 2014.
Written Opinion in International Application No. PCT/JP2013/081453, dated Feb. 10, 2014.
Written Opinion in International Patent Application No. PCT/JP2013/080347, dated Feb. 10, 2014.
Written Opinion in PCT/JP2013/081455, dated Feb. 10, 2014.
Written Opinion of ISA in International Application No. PCT/JP2013/082891, dated Feb. 18, 2014.
Extended European Search Report corresponding to EP13861857.4, dated Jun. 22, 2016.
Office Action in JP Application No. 2012-272362, dated Aug. 25, 2015.
Office Action in JP Application No. 2012-272390, dated Jun. 10, 2016.
Extended European Search Report in EP13862226.1, dated Jun. 21, 2016.
Office Action in CN Patent Application No. 201380065333.6 dated Jul. 31, 2017. 21pp.
Office Action in CN Application No. 201380065247.5, dated Feb. 14, 2017.
Written Opinion of ISA in International Application No. PCT/JP2013/081454, dated Feb. 10, 2014.
Extended European Search Report in EP Application No. 13862655.1, dated Aug. 1, 2016.
Office Action in U.S. Appl. No. 14/651,227, dated Jun. 12, 2017.
Office Action in U.S. Appl. No. 14/651,228, dated Jun. 1, 2017.
Office Action in U.S. Appl. No. 14/651,229, dated Jun. 2, 2017.
Office Action in U.S. Appl. No. 14/651,231, dated May 30, 2017.
Office Action in U.S. Appl. No. 14/651,667, dated Jun. 13, 2017.
Office Action in U.S. Appl. No. 14/651,668, dated Jun. 13, 2017.
Notice of Allowance in U.S. Appl. No. 14/651,648, dated May 30, 2017.
Office Action in CN Patent Application No. 201380065627.9, dated Jul. 20, 2017. 15pp.
Office Action in U.S. Appl. No. 14/651,666, dated Jul. 11, 2017. 15pp.
Notice of Allowance in U.S. Appl. No. 14/651,648, dated Aug. 23, 2017. 11pp.
Office Action in CN Patent Application No. 201380065150.4, dated Dec. 28, 2016. 11pp.
Office Action in U.S. Appl. No. 14/651,669, dated Oct. 10, 2017. 16pp.
Office Action in U.S. Appl. No. 14/651,228, dated Sep. 27, 2017. 24pp.
Office Action in U.S. Appl. No. 14/651,229, dated Sep. 27, 2017. 15pp.
Office Action in U.S. Appl. No. 14/651,231, dated Sep. 21, 2017. 13pp.
Office Action in CN Application No. 201380065183.9, dated Aug. 21, 2017. 17pp.
Notice of Allowance in U.S. Appl. No. 14/651,668, dated Oct. 5, 2017. 8pp.
Notice of Allowance in U.S. Appl. No. 14/651,227, dated Oct. 6, 2017. 20pp.
Notice of Allowance in U.S. Appl. No. 14/651,667, dated Oct. 17, 2017. 20pp.
Supplemental Notice of Allowability in U.S. Appl. No. 14/651,668, dated Nov. 8, 2017, 5pp.

* cited by examiner

DISPOSABLE DIAPER FOR PETS

RELATED APPLICATIONS

The present application is a National Phase of International Application Number PCT/JP2013/080951, filed Nov. 15, 2013, and claims priority of Japanese Patent Application No. 2012-272362 filed on Dec. 13, 2012.

TECHNICAL FIELD

The present invention relates to a disposable diaper for pets, and more particularly to a disposable diaper for pets that fits well around the legs of the pet.

BACKGROUND ART

It is common to keep pets, typically dogs and cats, indoors. Therefore, various kinds of disposable diapers for pets are available. For example, a disposable diaper for pets as disclosed in Japanese Unexamined Patent Application Publication JP 2004-159591A is provided.

PRIOR ART DOCUMENT

Patent Document

Patent Document 1:
JP 2004-159591A

SUMMARY OF THE INVENTION

Problem to be Solved by the Invention

The disposable diaper for pets (disposable pet diaper) disclosed in JP2004-159591A is now described with reference to FIGS. 25 and 26. FIG. 25 is a plan view showing the disposable pet diaper in its unfolded state, and FIG. 26 is an explanatory drawing for illustrating a state of the disposable pet diaper worn by a pet.

A disposable pet diaper 1000 includes a liquid-permeable sheet 9910, a liquid-resistant sheet (not shown) and an absorbent core 2000 disposed between the liquid-permeable sheet 9910 and the liquid-resistant sheet.

The liquid-permeable sheet 9910 is formed of liquid-permeable nonwoven fabric. The liquid-resistant sheet is formed of liquid-impermeable plastic film. The absorbent core 2000 is formed of a mixture of liquid absorbent fibers such as pulp, and a super absorbent polymer.

The disposable pet diaper 1000 has an abdomen-side waist area 1110, a back-side waist area 1130 and a crotch area 1120 between the abdomen-side waist area 1110 and the back-side waist area 1130.

The disposable pet diaper 1000 has a diaper longitudinal direction in which the abdomen-side waist area 1110, the crotch area 1120 and the back-side waist area 1130 are contiguously formed, and a diaper transverse direction crossing the diaper longitudinal direction.

The abdomen-side waist area 1110 has an end 1110A and the back-side waist area 1130 has an end 1130A in the diaper longitudinal direction.

An abdomen-side flap 1150 is formed in the abdomen-side waist area 1110 and has a back-side end 1150B. The back-side end 1150B is contiguously formed to extend from an end of the abdomen-side flap 1150 in the diaper transverse direction to a region of an end 2220 of the absorbent core 2000 in the diaper transverse direction.

When the disposable pet diaper 1000 is put on a pet, a relatively long area of the abdomen-side flap 1150 comes in contact with a leg α1 of the pet.

A fastening part 3000 having a plurality of hooks is provided on the abdomen-side flap 1150.

The absorbent core 2000 is disposed in a prescribed region extending over the abdomen-side waist area 1110 and the crotch area 1120. A tail insertion opening 1190 is formed in a prescribed position in the crotch area 1120 and the back-side waist area 1130 where the absorbent core 2000 is not provided.

A fastening region 9000 comprising a target tape is formed in a prescribed position of the back-side waist area 1130. In order to put the disposable pet diaper 1000 on a pet, the hooks on the fastening part 3000 are engaged with the fastening region 9000.

A back-side flap 1160 is formed in the back-side waist area 1130.

A leg stretchable elastic member 4000 is provided in the vicinity of an end of the disposable pet diaper 1000 in the diaper transverse direction. Leg gathers 4410 shown in FIG. 26 are formed by contraction of the leg stretchable elastic member 4000. The leg stretchable elastic member 4000 is arranged to extend over part of the abdomen-side waist area 1110 and the crotch area 1120. Therefore, the contraction force of the leg stretchable elastic member 4000 has no influence on the end 1110A of the abdomen-side waist area 1110 and the end 1130A of the back-side waist area 1130.

A leakproof sheet 8000 is arranged to extend inward from the end in the diaper transverse direction of the disposable pet diaper 1000. A leakproof sheet stretchable elastic member 6000 is provided in the leakproof sheet 8000. Leakproof gathers and a leakproof wall which are not shown are formed by contraction of the leakproof sheet stretchable elastic member 6000.

An end of the leakproof sheet stretchable elastic member 6000 in the abdomen-side waist area does not extend up to the end 1110A of the disposable pet diaper 1000 in the diaper longitudinal direction. The back-side end of the leakproof sheet stretchable elastic member 6000 is arranged to extend beyond the tail insertion opening 1190.

In order to put the disposable pet diaper 1000 on a pet, the back-side waist area 1130 is placed on a back of the pet and the crotch area 1120 and the abdomen-side waist area 1110 are placed on a crotch and an abdomen of the pet, and then the fastening part 3000 is fastened to the fastening region 9000.

At this time, as described above, the length with which the end 1150B of the abdomen-side flap 1150 comes in contact with a leg of the pet is relatively long.

Therefore, the end 1150B may be turned up when the diaper is put on the pet. As a result, the pet may dislike wearing the disposable pet diaper 1000, or excrement may leak out.

Accordingly, it is an object of the present invention to provide a disposable diaper for pets which fits well around the legs of the pet.

Means for Solving the Problem

According to the present invention, a disposable diaper for pets is provided which includes a back-side waist area, an abdomen-side waist area, and a crotch area between the back-side waist area and the abdomen-side waist area, a flap formed in the abdomen-side waist area and having an end on the back side, a diaper longitudinal direction in which the back-side waist area, the crotch area and the abdomen-side waist area contiguously extend when the disposable diaper is not worn by a pet, and a diaper transverse direction crossing the diaper longitudinal direction, both ends in the diaper longitudinal direction, and both ends in the diaper transverse direction, a diaper longitudinal center line extending in the diaper longitudinal direction and passing through a center of the disposable diaper in the diaper transverse direction, a diaper center point which bisects the diaper longitudinal center line on the disposable diaper, a tail insertion opening formed in a prescribed region in the diaper longitudinal direction, an absorbent core formed on one side of the tail insertion opening in the diaper longitudinal direction and disposed in a prescribed region extending over the crotch area and the abdomen-side waist area, a fastening part having a prescribed length and provided on the flap, a fastening part longitudinal direction in which the length of the fastening part extends and a fastening part transverse direction crossing the fastening part longitudinal direction, a fastening part midpoint which bisects a length of the fastening part in the fastening part transverse direction on a boundary between the fastening part and the flap, a fastening region provided in the back-side waist area and configured to receive the fastening part, and a shortest line point located on the diaper longitudinal center line at a shortest straight-line distance from the fastening part midpoint to the diaper longitudinal center line via the back-side end of the flap.

Further, the shortest line point is located on an abdomen-side waist area side beyond the diaper center point.

When the disposable diaper according to this invention is put on the pet, the crotch area and the abdomen-side waist area cover a crotch and an abdomen of the pet, while the back-side waist area is closely fitted to a back of the pet, and the fastening part is fastened to the fastening region.

Further, the weight of the absorbent core after excretion is received in the longitudinal direction of the fastening part while the disposable diaper according to this invention is worn by the pet.

In a further aspect of the solution according to the present invention, a straight-line distance between the shortest line point and a diaper end center point at which the end in the diaper longitudinal direction in the abdomen-side waist area and the diaper longitudinal center line intersect is 170 to 250 mm.

In a further aspect of the solution according to the present invention, the ratio of the straight-line distance between the shortest line point and the diaper end center point at which the end in the diaper longitudinal direction in the abdomen-side waist area and the diaper longitudinal center line intersect, to the straight-line distance between the abdomen-side end and the back-side end on the diaper longitudinal center line is 45.5 to 50.0%.

Effect of the Invention

In this invention, the back-side end of the abdomen-side flap is configured to reduce contact with a leg of a pet. Therefore, the disposable diaper for pets fits well around the legs of the pet.

BEST MODES FOR CARRYING OUT THE INVENTION

First Embodiment

A first embodiment of the present invention is now described with reference to FIGS. 1 to 15.

Figure 1:
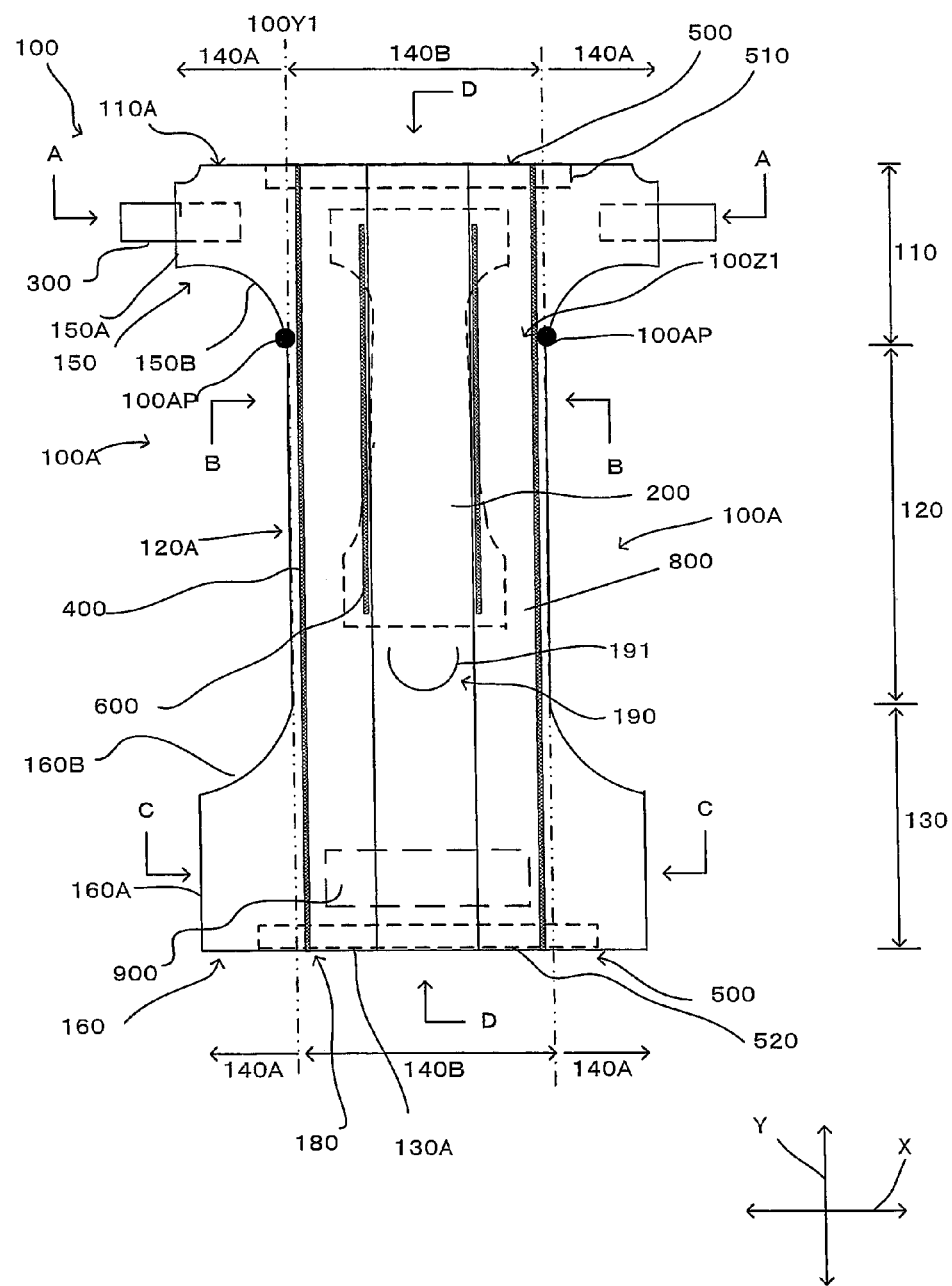
FIG. 1 is a plan view showing a disposable diaper for pets in its unfolded state according to a first embodiment of the present invention.

FIG. 1 is a plan view showing a disposable diaper for pets in its unfolded state. The "pet" in this embodiment widely includes vertebrates (mammals, reptiles, birds and amphibians) and invertebrates, and typically represents pets such as cats, dogs, rabbits, hamsters, horses, cows, pigs and goats. The term "unfolded state" as used in this embodiment refers to the state in which an unused disposable diaper is unfolded or opened and a contraction force of a stretchable elastic member is not developed.

A disposable diaper for pets (disposable pet diaper) 100 has an abdomen-side waist area 110, a back-side waist area 130 and a crotch area 120 between the abdomen-side waist area 110 and the back-side waist area 130. When the disposable pet diaper 100 is worn by a pet, the abdomen-side waist area 110, the back-side waist area 130 and the crotch area 120 are in contact with an abdomen, a back and a crotch of the pet, respectively.

The abdomen-side waist area 110, the back-side waist area 130 and the crotch area 120 are example embodiments that correspond to the "abdomen-side waist area, the back-side waist area and the crotch area between the abdomen-side waist area and the back-side waist area", respectively, according to this invention.

In the unfolded state as shown in FIG. 1, the disposable pet diaper 100 has a diaper longitudinal direction Y in which the abdomen-side waist area 110, the crotch area 120 and the back-side waist area 130 contiguously extend, and a diaper transverse direction X crossing the diaper longitudinal direction Y. The term "crossing" as used in this specification means "perpendicularly crossing" unless otherwise specified.

The diaper longitudinal direction Y and the diaper transverse direction X are example embodiments that correspond to the "diaper longitudinal direction in which the abdomen-side waist area, the crotch area and the back-side waist area contiguously extend when the disposable diaper is not worn by a pet, and a diaper transverse direction crossing the diaper longitudinal direction", respectively, according to this invention.

The disposable pet diaper 100 has an inside surface 100Z1 which faces a pet and an outside surface 100Z2 opposite to the inside surface 100Z1.

In this embodiment, the inside surface 100Z1 may also be referred to as a pet-side surface or a pet wearing surface.

The disposable pet diaper 100 has an end 110A formed in the abdomen-side waist area 110 and an end 130A formed in the back-side waist area 130 in the diaper longitudinal direction Y.

The ends 110A and 130A are an example embodiment that corresponds to the "both ends in the diaper longitudinal direction" according to this invention.

The disposable pet diaper 100 has a pair of ends 100A in the diaper transverse direction X. Each of the ends 100A contiguously extends over an end 150A in the diaper transverse direction and a back-side end 150B in each of the abdomen-side flaps 150, an end 160A in the diaper transverse direction and an abdomen-side end 160B in each of the back-side flaps 160, and a leg-side end 120A between the back-side end 150B of the abdomen-side flap 150 and the abdomen-side end 160B of the back-side flap 160.

The ends 100A are an example embodiment that corresponds to the "both ends in the diaper transverse direction" according to this invention.

The disposable pet diaper 100 has a tail insertion opening 190 formed in a prescribed region in the diaper longitudinal direction Y. The tail insertion opening 190 is formed by an arcuate cut 191 extending through the inside surface 100Z1 and the outside surface 100Z2.

Although, in the first embodiment, the tail insertion opening 190 is formed by the arcuate cut 191, it may be a circular opening formed by an annular cut.

The tail insertion opening 190 is an example embodiment that corresponds to the "tail insertion opening formed in a prescribed region in the diaper longitudinal direction" according to this invention.

The disposable pet diaper 100 has an absorbent core 200 formed on one side of the tail insertion opening 190 in the diaper longitudinal direction Y and disposed in a prescribed region extending over the crotch area 120 and the abdomen-side waist area 110. The absorbent core 200 has an abdomen-side end 210, a back-side end 220 and a pair of ends 230 in the diaper transverse direction.

The absorbent core 200 is formed of a mixture of a particulate or fibrous super absorbent polymer and fluff pulp or a mixture of a particulate or fibrous super absorbent polymer, fluff pulp and thermoplastic synthetic resin fibers. Preferably, in order to prevent deformation of the absorbent core 200 and falling off of the super absorbent polymer, the absorbent core 200 may be entirely covered with a liquid-permeable sheet such as tissue paper and hydrophilic fiber nonwoven fabric. Further, preferably, the absorbent core 200 may be compressed into a prescribed thickness in the manufacturing process. As the super absorbent polymer, synthetic polymer-based, starch-based or cellulose-based polymer can be appropriately used.

The absorbent core 200 is an example embodiment that corresponds to the "absorbent core formed on one side of the tail insertion opening in the diaper longitudinal direction and disposed in a prescribed region extending over the crotch area and the abdomen-side waist area" according to this invention.

Figure 2:
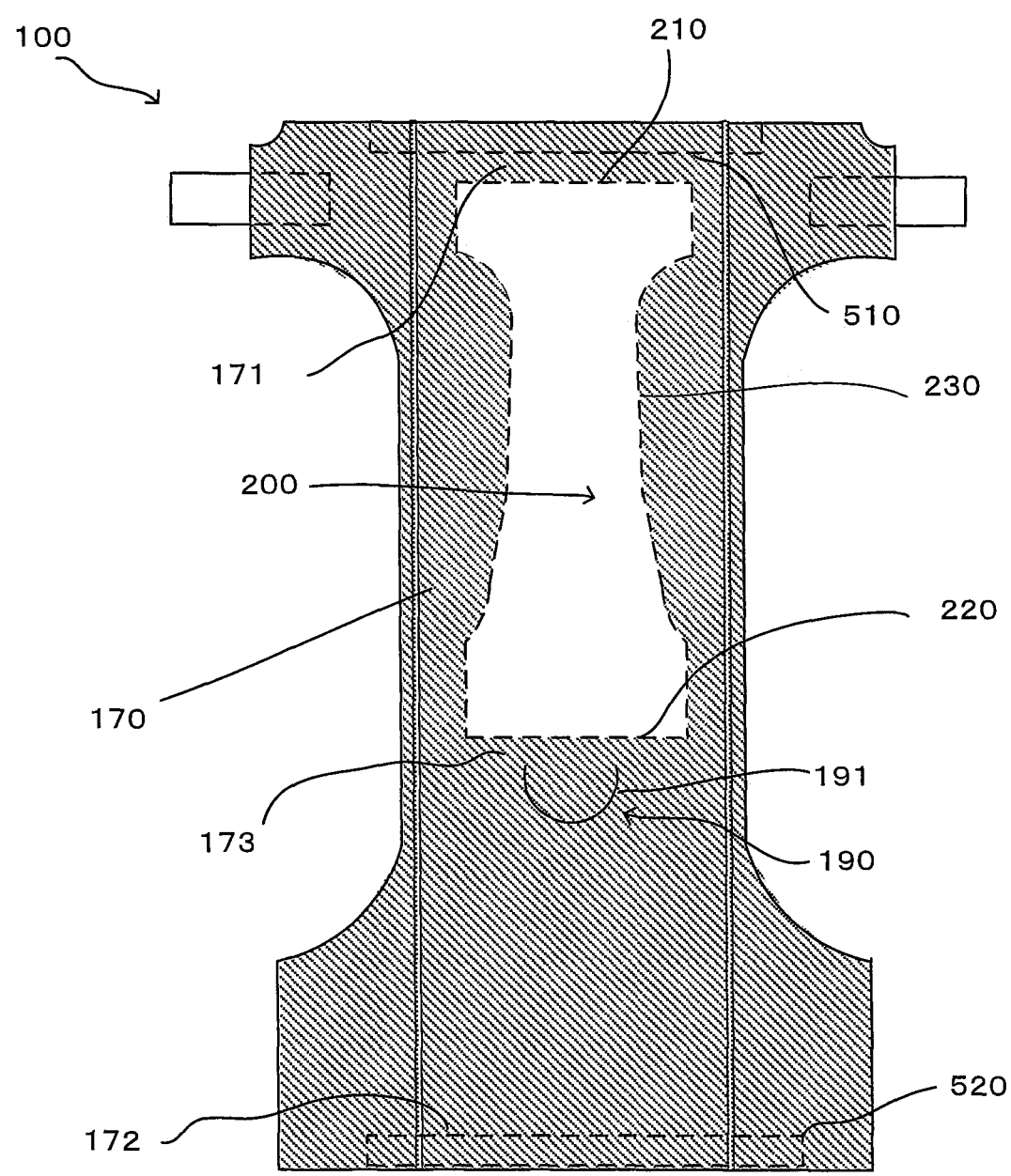
FIG. 2 is a plan view for showing an absorbent-core non-arrangement region in the unfolded state of the disposable diaper.

As shown in FIG. 2, a region of the disposable pet diaper 100 in which the absorbent core 200 is not disposed is referred to as an absorbent-core non-arrangement region 170.

In the absorbent-core non-arrangement region 170, regions adjacent to the abdomen-side end 210 and the back-side end 220 of the absorbent core 200 and to the back-side end 130A of the disposable pet diaper 100 each form an erected region for forming an erected section 700 which is described below. Specifically, the region adjacent to the abdomen-side end 210 of the absorbent core 200, the region adjacent to the back-side end 220 of the absorbent core 200, and the region adjacent to the back-side end 130A of the disposable pet diaper 100 are referred to as an abdomen-side erected region 171, a crotch-side erected region 173 and a back-side erected region 172, respectively.

Depending on design of the disposable pet diaper 100, part of the absorbent core 200 may be arranged within the absorbent-core non-arrangement region 170, especially in any of the erected regions. Specifically, part of tissue paper, pulp fibers or super absorbent polymer may be disposed in the erected region. Even in such a case, if the erected region maintains its flexibility and forms the erected section 700, the absorbent-core non-arrangement region 170 is considered as being substantially formed and the erected region is also considered as being formed at the same time.

The disposable pet diaper 100 has fastening parts 300 on the both ends 150A of the abdomen-side flap 150 in the diaper transverse direction.

Figure 3:
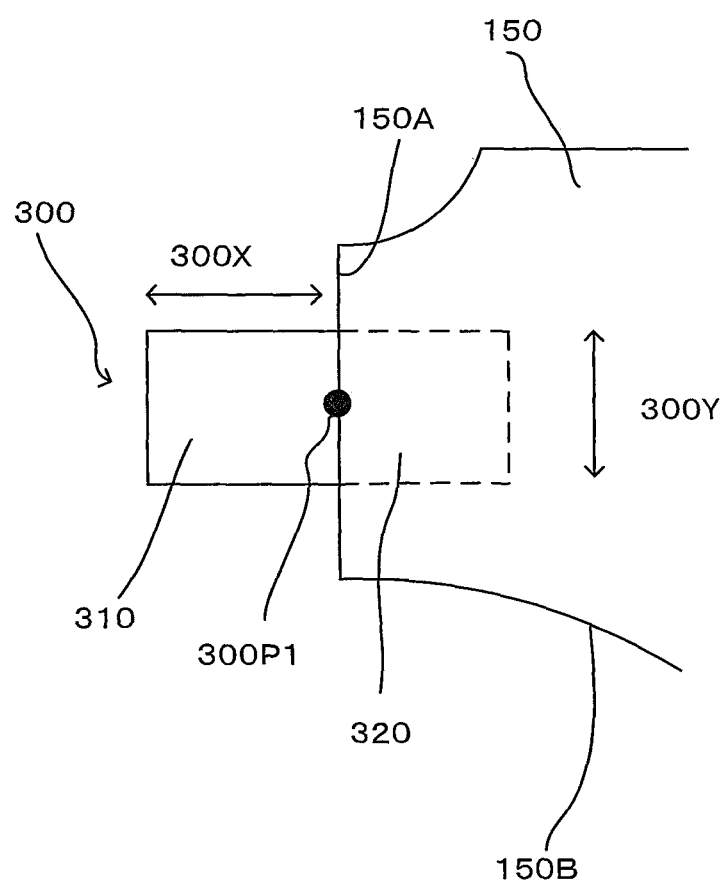
FIG. 3 is a plan view for showing a structure of an abdomen-side flap.

As shown in FIG. 3, each of the fastening parts 300 has a fastening part longitudinal direction 300X and a fastening part transverse direction 300Y. In the fastening part longitudinal direction 300X, the fastening part 300 has a fixed part 320 in which the fastening part 300 is fixed to the disposable pet diaper 100, and a free part 310 provided to be fastened to a fastening region 900.

The fastening part 300 is a fiber nonwoven fabric made of polyolefin thermoplastic synthetic fibers, or a plastic film made of polyolefin thermoplastic synthetic resin. A plurality of hooks (not shown) are provided on the diaper inside surface 100Z1 of the free part 310. The hooks are formed of polyolefin thermoplastic synthetic resin. Although the hooks here are provided and configured to be fastened to the fastening region 900, other structures such as an adhesive can be selected for use in place of the hooks, depending on the structure of the fastening region 900.

The fastening part 300 is an example embodiment that corresponds to the "fastening part having a prescribed length and provided on the abdomen-side waist area" according to this invention.

The fastening part longitudinal direction 300X is an example embodiment that corresponds to the "fastening part longitudinal direction in which the length of the fastening part extends" according to this invention.

The fastening part transverse direction 300Y is an example embodiment that corresponds to the "fastening part transverse direction crossing the fastening part longitudinal direction" according to this invention.

The disposable pet diaper 100 has flaps 140A. The flaps 140A include a pair of abdomen-side flaps 150 formed on the both ends 100A in the diaper transverse direction in the abdomen-side waist area 110, and a pair of back-side flaps 160 formed on the both ends 100A in the diaper transverse direction in the back-side waist area 130. The flaps 140A are defined by a pair of virtual lines 100Y1 extending in the diaper longitudinal direction and passing through a pair of minimum width points 100AP on the ends 100A of the disposable pet diaper 100 in the diaper transverse direction between which a line connecting the ends 100A in the diaper transverse direction is shortest. Specifically, the virtual lines 100Y1 are referred to as flap boundary lines, and regions outside a pair of the flap boundary lines 100Y1 are referred to as flaps (the abdomen-side flaps 150, the back-side flaps 160), while an inside region between the flap boundary lines is referred to as a body 140B.

As shown in FIG. 3, in the abdomen-side flap 150, the free end 310 of the fastening part 300 protrudes from the end 150A in the diaper transverse direction. A point which bisects the fastening part 300 in the fastening part transverse direction 300Y on a boundary between the end 150A and the fastening part 300 is referred to as a fastening part midpoint 300P1.

The back-side end 150B of the abdomen-side flap 150 is arcuately formed and extends contiguously from the end 150A of the abdomen-side flap 150 in the diaper transverse direction to the leg-side end 120A.

The abdomen-side flap 150 is an example embodiment that corresponds to the "flap formed in the abdomen-side waist area and having an end on the back side" according to this invention.

Further, the fastening part midpoint 300P1 is an example embodiment that corresponds to the "fastening part midpoint which bisects a length of the fastening part in the fastening part transverse direction on a boundary between the fastening part and the flap" according to this invention.

A preferable structure of the abdomen-side flap 150 is now described with reference to FIGS. 4 and 5.

Figure 4:
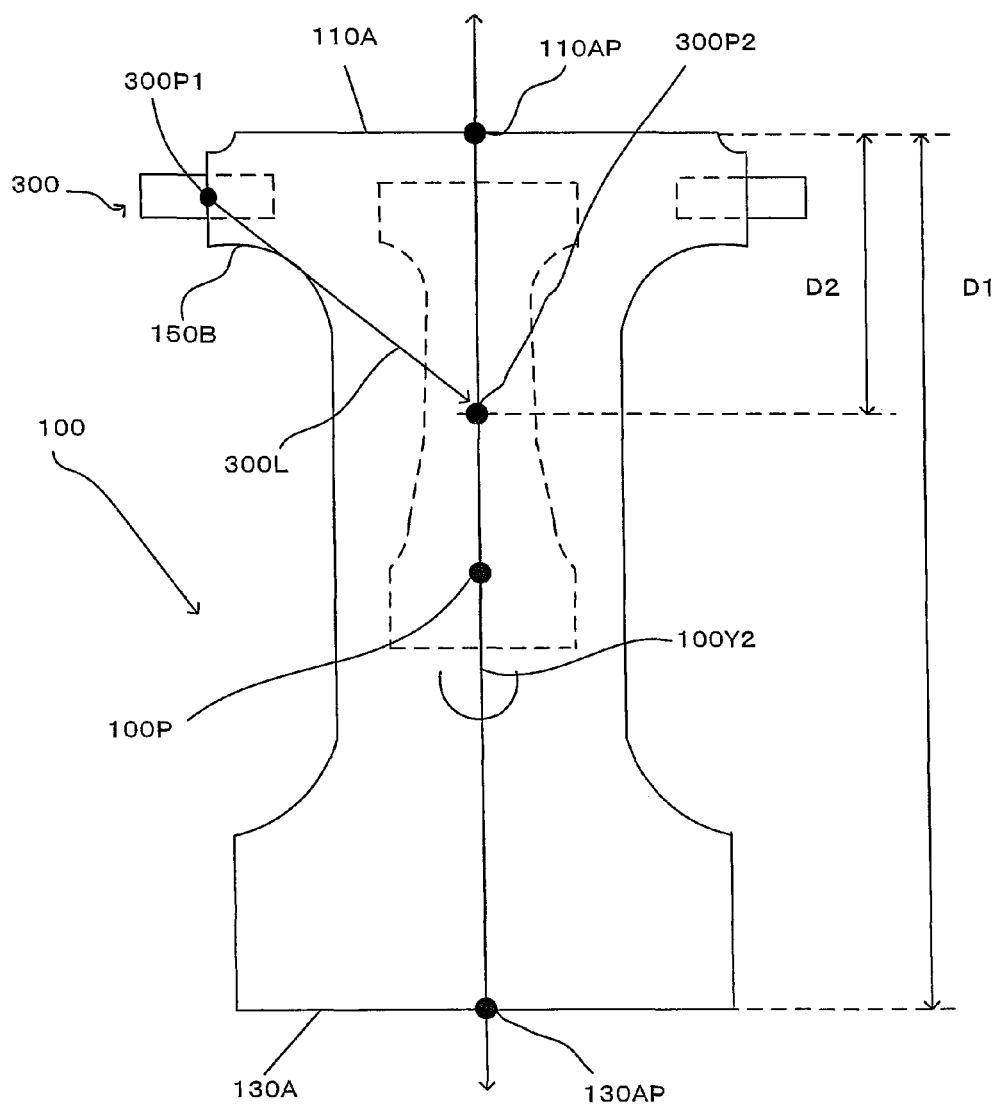
FIG. 4 is an explanatory drawing regarding to measurement for specifying a preferable structure of the abdomen-side flap.

In FIG. 4, a diaper longitudinal center line 100Y2 passes through the center of the disposable pet diaper 100 in the diaper transverse direction X. Specifically, the diaper longitudinal center line 100Y2 coincides with a line connecting an abdomen-side end center point 110AP on the center of the abdomen-side end 110A and a back-side end center point 130AP on the center of the back-side end 130A in the disposable pet diaper 100.

The diaper longitudinal center line 100Y2 is an example embodiment that corresponds to the "diaper longitudinal center line extending in the diaper longitudinal direction and passing through a center of the disposable diaper in the diaper transverse direction" according to this invention.

The distance between the abdomen-side end 110A and the back-side end 130A on the diaper longitudinal center line 100Y2 is referred to as a diaper longitudinal length D1.

The diaper longitudinal length D1 is an example embodiment that corresponds to the "straight-line distance between the abdomen-side end and the back-side end on the diaper longitudinal center line" according to this invention.

Further, a point which bisects the diaper longitudinal length D1 is referred to as a diaper center point 100P.

The diaper center point 100P is an example embodiment that corresponds to the "diaper center point which bisects the diaper longitudinal center line on the disposable diaper" according to this invention.

In providing the structure of the abdomen-side flap 150, the inventor focused on the relation between straight lines connecting the fastening part midpoint 300P1 of the fastening part 300 and the diaper longitudinal center line 100Y2 and the shape of the back-side end 150B of the abdomen-side flap 150.

Especially, the relation between a shortest straight-line distance 300L of a straight line passing the back-side end 150B of the abdomen-side flap 150, among the straight lines connecting the fastening part midpoint 300P1 of the fastening part 300 and the diaper longitudinal center line 100Y2, and a point of intersection of this straight line with the diaper longitudinal center line 100Y2 or a shortest line point 300P2 was focused on.

The shortest line point 300P2 is an example embodiment that corresponds to the "shortest line point located on the diaper longitudinal center line at a shortest straight-line distance from the fastening part midpoint to the diaper longitudinal center line via the back-side end of the flap" according to this invention.

As a result of keen studies, it was found that the abdomen-side flap 150 has a suitable and advantageous structure when the shortest line point 300P2 is located on the abdomen-side end 110A side of the disposable pet diaper 100 beyond the diaper center point 100P.

This suitable structure of the abdomen-side flap 150 is an example embodiment that corresponds to the structure that "the shortest line point is located on an abdomen-side waist area side beyond the diaper center point" according to this invention.

Specifically, the position of the shortest line point 300P2 has a great influence on the shape of the back-side end 150B of the abdomen-side flap 150. As described above, the back-side end 150B is arcuate and extends from the end 150A of the abdomen-side flap 150 in the diaper transverse direction to the leg-side end 120A of the disposable pet diaper 100.

In this respect, assuming that the shortest line point 300P2 is located on the back-side end 130A side beyond the diaper center point, the position at which the back-side end 150B of the abdomen-side flap 150 meets the leg-side end 120A is located closer to the back-side end 130A than that in the present invention. As a result, the area of the abdomen-side flap 150 is increased. Therefore, when the disposable pet diaper 100 is put on a pet α, a longer area of the abdomen-side flap 150 comes in contact with a leg α1 of the pet.

Figure 5:
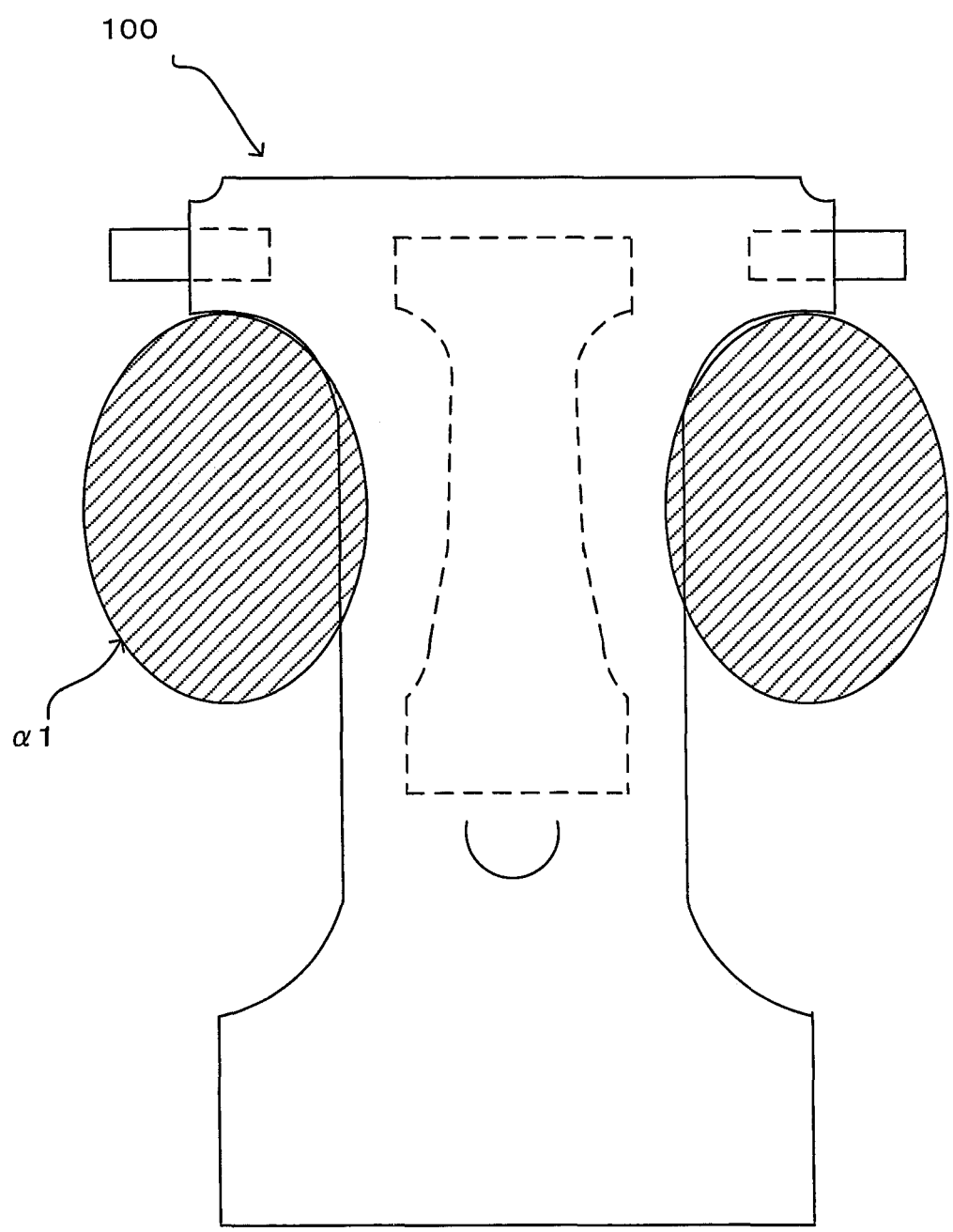
FIG. 5 is an explanatory drawing for illustrating the relation between the disposable diaper and legs of the pet

In the position of the shortest line point 300P2 according to this invention, however, as shown in FIG. 5, the area of the abdomen-side flap 150 can be reduced, and the length with which the abdomen-side flap 150 comes in contact with the leg α1 of the pet can be reduced.

The disposable pet diaper 100 is available in various sizes corresponding to pets of various sizes. The pets here are limited to cats and dogs. In this case, when a measured length D2 or a distance between the shortest line point 300P2 and the abdomen-side end center point 110AP of the disposable pet diaper 100, is set to 170 to 250 mm, the suitable and advantageous abdomen-side flap 150 can be provided in the disposable pet diaper 100 of any size.

This is an example embodiment that corresponds to the feature that "a straight-line distance between the shortest line point and a diaper end center point at which the end in the diaper longitudinal direction in the abdomen-side waist area and the diaper longitudinal center line intersect is 170 to 250 mm" according to this invention.

Further, the relation between the measured length D2 and the diaper longitudinal length D1 of the disposable pet diaper 100 was also considered. As a result, it was found that the suitable and advantageous abdomen-side flap 150 can be provided in the disposable pet diaper 100 of any size when the ratio of the measured length D2 to the diaper longitudinal length D1 is 45.5 to 50.0%.

This is an example embodiment that corresponds to the feature that "a ratio of a straight-line distance between the shortest line point and the diaper end center point at which the end in the diaper longitudinal direction in the abdomen-side waist area and the diaper longitudinal center line intersect, to a straight-line distance between the abdomen-side end and the back-side end on the diaper longitudinal center line is 45.5 to 50.0%" according to this invention.

The disposable pet diaper 100 has the fastening region 900 which is removably fastened to the fastening part 300.

The fastening region 900 is adhered to the outside surface 100Z2 in the back-side waist area 130. The fastening region 900 is formed by a target tape which is a fiber nonwoven fabric made of polyolefin thermoplastic synthetic fibers, or a plastic film made of polyolefin thermoplastic synthetic resin, and having a large number of loops (not shown) made of polyolefin thermoplastic synthetic resin. Depending on the structure of the hooks in the free part 310 of the fastening part 300, it may be constructed without using the target tape such that the fastening part 300 can be directly fastened to the nonwoven fabric forming the diaper outside surface 100Z2. In this case, the fastening region 900 is provided and configured as a region to which the fastening part 300 can be fastened in the nonwoven fabric forming the diaper outside surface 100Z2. Further, in the case of the structure in which an adhesive is used in the free part 310 of the fastening part 300, a plastic film is used as the fastening region 900.

The fastening region 900 is an example embodiment that corresponds to the "fastening region provided in the back-side waist area and configured to receive the fastening part" according to this invention.

In the disposable pet diaper 100, a leg stretchable elastic member 400 is provided in the absorbent-core non-arrangement region 170 between the end 100A in the diaper transverse direction and the absorbent core 200.

The leg stretchable elastic member 400 is arranged in a stretched state, and when using the disposable pet diaper 100, the leg stretchable elastic member 400 contracts to form leg gathers 410 which are described below.

The leg stretchable elastic member 400 is arranged to extend from the abdomen-side end 110A to the back-side end 130A of the disposable pet diaper 100 in the diaper longitudinal direction Y.

Here, "to extend from the abdomen-side end 110A to the back-side end 130A" of the disposable pet diaper 100 does not only mean that the leg stretchable elastic member 400 continuously extends from the abdomen-side end 110A to the back-side end 130A. Specifically, the leg stretchable elastic member 400 may be arranged to extend with a distance from the abdomen-side end 110A or the back-side end 130A only if the abdomen-side end 110A or the back-side end 130A is acted upon by the contraction force of the leg stretchable elastic member 400 and the erected section 700 is formed.

The leg stretchable elastic member 400 is formed of synthetic or natural rubber thread.

The disposable pet diaper 100 has a waist stretchable elastic member 500. The waist stretchable elastic member 500 includes an abdomen-side waist stretchable elastic member 510 disposed in the absorbent-core non-arrangement region 170 between the diaper longitudinal end 110A and the abdomen-side end 210 of the absorbent core 200, and a back-side waist stretchable elastic member 520 disposed in the absorbent-core non-arrangement region 170 between the diaper longitudinal end 130A and the back-side end 220 of the absorbent core 200.

The waist stretchable elastic member 500 is arranged in a stretched state, and when using the disposable pet diaper 100, the waist stretchable elastic member 500 contracts to form waist gathers 530.

The waist stretchable elastic member 500 and the leg stretchable elastic member 400 are arranged to overlap each other. Here, the term "overlap" as used in this embodiment does not only mean that the waist stretchable elastic member 500 and the leg stretchable elastic member 400 are in direct contact with each other. Specifically, the waist stretchable elastic member 500 and the leg stretchable elastic member 400 do not need to be in direct contact with each other only if their contraction forces act upon each other such that a contraction force intersecting region 180 is formed.

The waist stretchable elastic member 500 is formed of a urethane foamed sheet material.

The disposable pet diaper 100 has a leakproof sheet 800. A leakproof sheet stretchable elastic member 600 is disposed in a stretched state in the leakproof sheet 800.

The leakproof sheet 800 is disposed in a prescribed region extending from each of the ends 100A in the diaper transverse direction of the disposable pet diaper 100 to the body 140B of the disposable pet diaper 100.

The leakproof sheet stretchable elastic member 600 is disposed within a space which is created by a folded part 810 of an inner end of the leakproof sheet 800 and extends in the diaper longitudinal direction Y.

Figure 6:
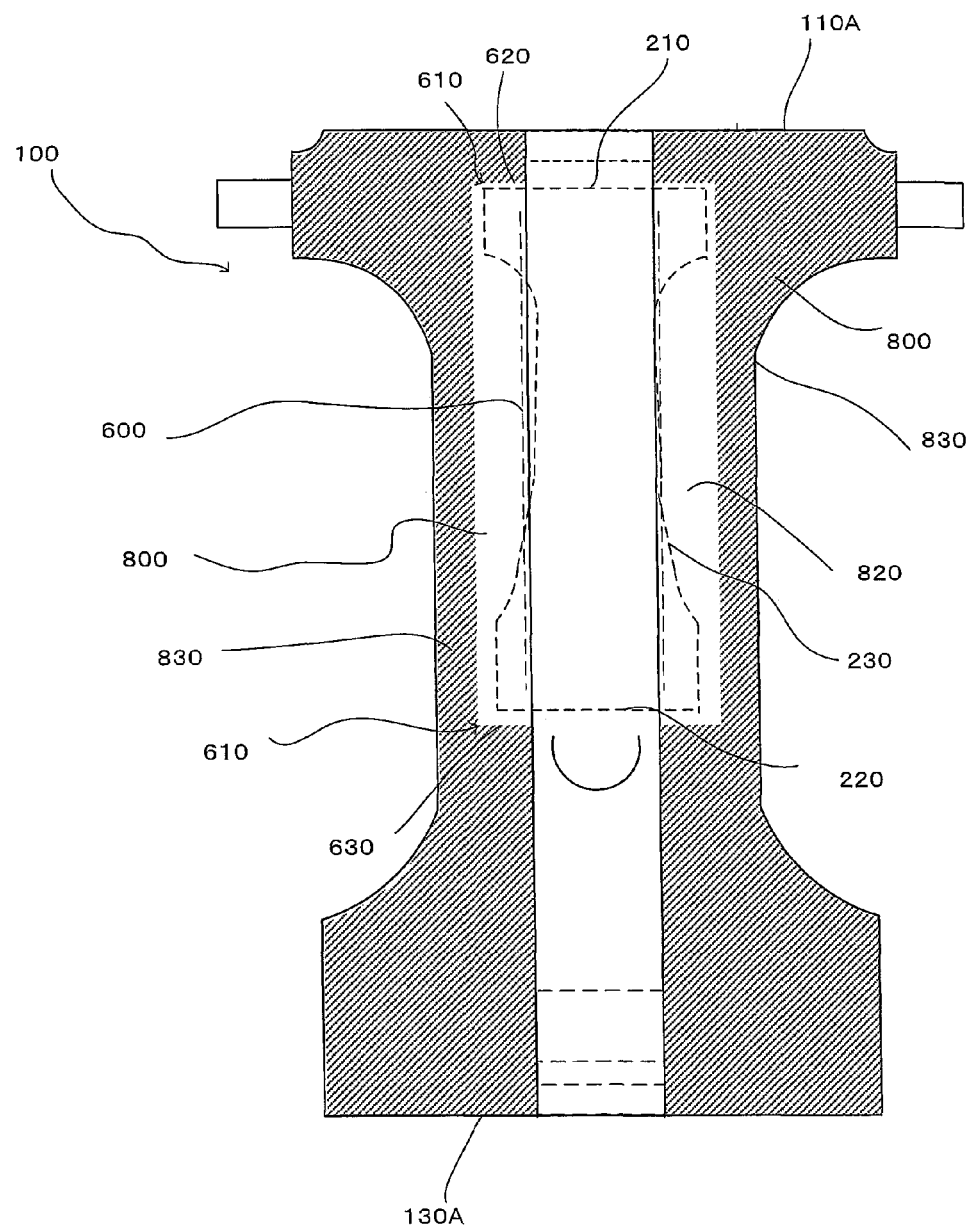
FIG. 6 is a plan view for showing a leakproof sheet fixed part in the unfolded state of the disposable diaper.

As shown in FIG. 6, the leakproof sheet 800 has a fixed part 830 which is fixed to other components (a liquid-permeable sheet 910, a liquid-resistant sheet 920, an outer sheet 930) of the disposable pet diaper 100 by an adhesive (not shown). In FIG. 6, the fixed part 830 is shown by hatching.

The fixed part 830 is not formed in a region of the leakproof sheet 800 which extends in the diaper longitudinal direction Y and overlaps with the end 230 of the absorbent core 200 in the diaper transverse direction X. This region not having the fixed part 830 is erected by contraction of the leakproof sheet stretchable elastic member 600 and forms a leakproof wall 820 which is described below. Further, leakproof gathers 840 are formed in the leakproof sheet 800 by contraction of the leakproof sheet stretchable elastic member 600.

The leakproof sheet stretchable elastic member 600 does not need to be provided along the whole length of the region (which forms the leakproof wall 820) not having the fixed part 830 in the diaper longitudinal direction Y. For example, it is sufficient to provide the leakproof sheet stretchable elastic member 600 only in part of the region of the leakproof wall 820 in the diaper longitudinal direction Y. Specifically, it is sufficient for the contraction force of the leakproof sheet stretchable elastic member 600 to act upon a part of the fixed part 830 on the both ends of the region of the leakproof wall 820 in the diaper longitudinal direction Y. Here, the part of the fixed part 830 on the both ends of the region of the leakproof wall 820 in the diaper longitudinal direction Y is referred to as a contraction force fixing part 610.

The contraction force fixing part 610 includes an abdomen-side contraction force fixing part 620 and a back-side contraction force fixing part 630.

The back-side contraction force fixing part 630 is provided between the back-side end 220 of the absorbent core 200 and the tail insertion opening 190. Specifically, by provision of this structure, the absorbent-core non-arrangement region 170 between the back-side end 220 of the absorbent core 200 and the tail insertion opening 190 is erected by contraction of the leakproof sheet stretchable elastic member 600 and forms the erected section 700.

Further, the abdomen-side contraction force fixing part 620 is provided between the abdomen-side end 210 of the absorbent core 200 and the abdomen-side end 110A of the disposable pet diaper 100. Specifically, by provision of this structure, as described below, the absorbent-core non-arrangement region 170 between the abdomen-side end 210 of the absorbent core 200 and the abdomen-side end 110A of the disposable pet diaper 100 is erected by contraction of the leakproof sheet stretchable elastic member 600 and forms the erected section 700.

The disposable pet diaper 100 includes the liquid-permeable sheet 910, the absorbent core 200, the liquid-resistant sheet 920, the outer sheet 930 and the leakproof sheet 800.

Figure 7:
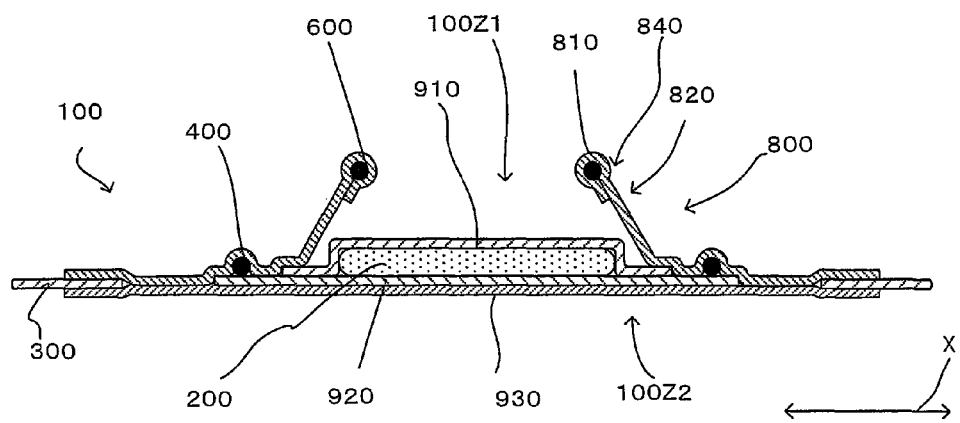
FIG. 7 is a sectional view taken along line A-A in FIG. 1.
Figure 8:
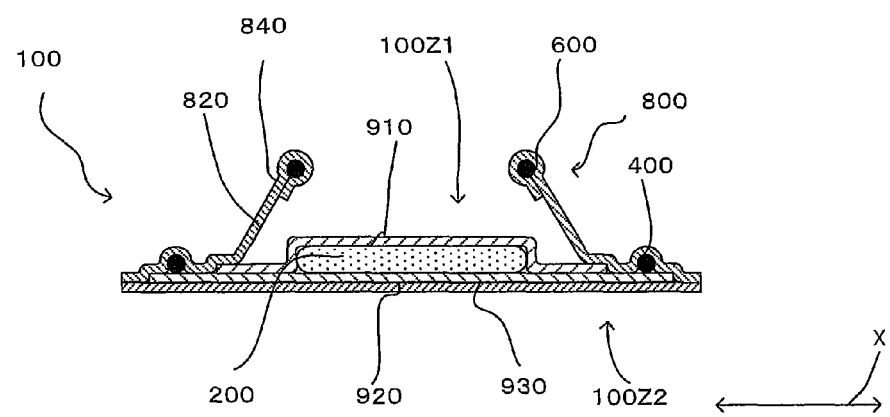
FIG. 8 is a sectional view taken along line B-B in FIG. 1.
Figure 9:
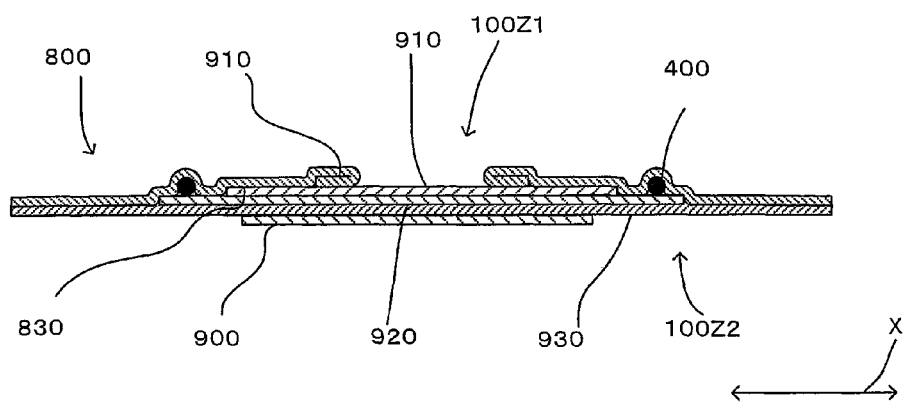
FIG. 9 is a sectional view taken along line C-C in FIG. 1.

As shown in FIGS. 7 to 9, the liquid-permeable sheet 910 is disposed on the inside surface 100Z1 side of the disposable pet diaper 100. The absorbent core 200 is disposed between the liquid-permeable sheet 910 and the liquid-resistant sheet 920. The outer sheet 930 is disposed on the outside surface 100Z2 side of the liquid-resistant sheet 920. The leakproof sheet 800 is disposed over the liquid-permeable sheet 910, the liquid-resistant sheet 920 and the outer sheet 930 in the diaper transverse direction X. As a result, the abdomen-side flap 150 and the back-side flap 160 are formed by the leakproof sheet 800 and the outer sheet 930.

The leg stretchable elastic member 400 is disposed between the leakproof sheet 800 and the liquid-resistant sheet 920.

The leakproof sheet stretchable elastic member 600 is disposed in the space inside the folded part 810 formed on the end of the leakproof sheet 800.

As shown in FIG. 7, the fastening part 300 is disposed between the leakproof sheet 800 and the outer sheet 930.

As shown in FIGS. 7 and 8, the leakproof sheet 800 not having the fixed part 830 is erected by contraction of the leakproof sheet stretchable elastic member 600 and forms the leakproof wall 820. At this time, a large number of creases or the leakproof gathers 840 are formed in the leakproof sheet 800.

As shown in FIG. 9, the fastening region 900 is provided on the outside surface 100Z2 of the outer sheet 930.

The waist stretchable elastic member 500, not shown, is disposed between the liquid-permeable sheet 910 and the liquid-resistant sheet 920.

The liquid-permeable sheet 910, the liquid-resistant sheet 920, the outer sheet 930 and the leakproof sheet 800 are formed of nonwoven fabric. The nonwoven fabric can be selected from those manufactured by spun lacing, needle punching, melt blowing, thermal bonding, spun bonding or chemical bonding.

An adhesive, not shown, is used to fix the liquid-permeable sheet 910, the liquid-resistant sheet 920, the outer sheet 930 and the leakproof sheet 800 with each other and to fix the leg stretchable elastic member 400, the leakproof sheet stretchable elastic member 600 and the waist stretchable elastic member 500. A hot-melt adhesive is preferably used as the adhesive, but other adhesives such as acrylic adhesive and rubber adhesive can also be used.

The adhesive is preferably applied in any one of spiral, wave, dot and stripe patterns.

Figure 10:
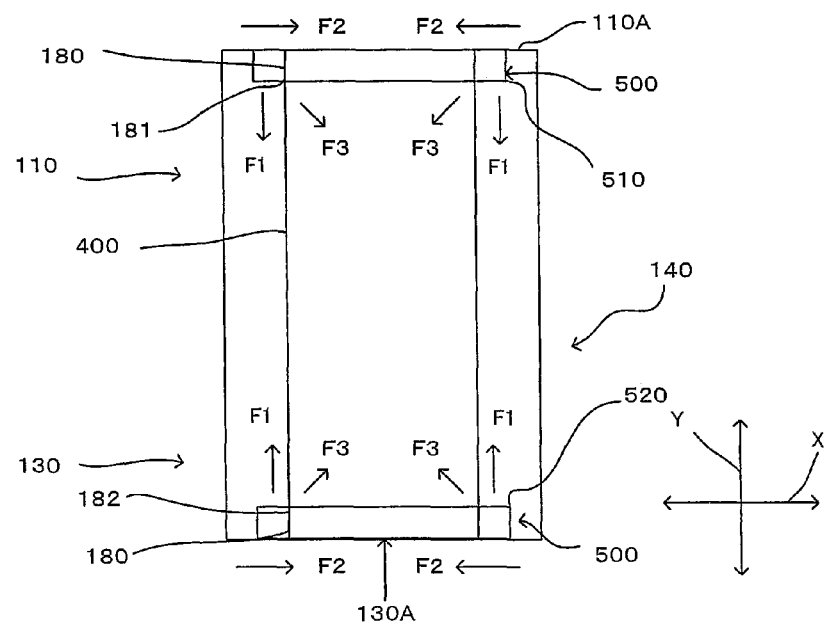
FIG. 10 is an explanatory drawing for illustrating the structure of a leg stretchable elastic member and a waist stretchable elastic member.
Figure 11:
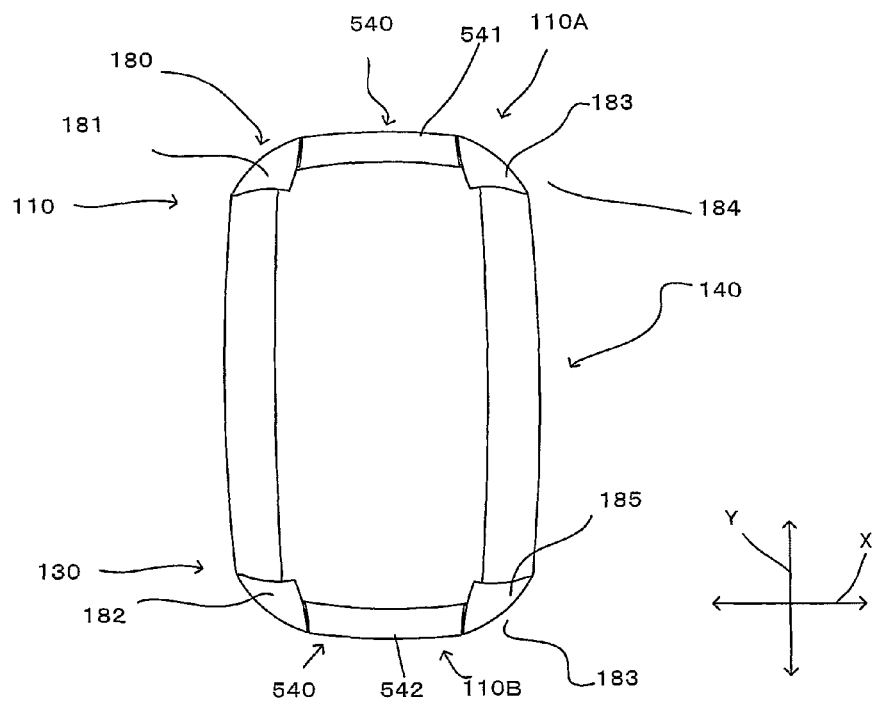
FIG. 11 is an explanatory drawing for illustrating the operation of the leg stretchable elastic member and the waist stretchable elastic member.

Next, the relation between the contraction forces of the leg stretchable elastic member 400 and the waist stretchable elastic member 500 is described with reference to FIGS. 10 and 11. In FIGS. 10 and 11, for convenience of explanation, the abdomen-side flaps 150 and the back-side flaps 160 are not shown and only the body 140B is shown.

As shown in FIG. 10, the leg stretchable elastic member 400 contracts inward from the ends in the diaper longitudinal direction Y. Specifically, contraction force F1 of the leg stretchable elastic member 400 acts inward in the diaper longitudinal direction Y.

The waist stretchable elastic member 500 contracts inward from the ends in the diaper transverse direction X. Specifically, contraction force F2 of the waist stretchable elastic member 500 acts inward in the diaper transverse direction X.

The contraction force intersecting region 180 is a region in which the contraction force F1 of the leg stretchable elastic member 400 and the contraction force F2 of the waist stretchable elastic member 500 intersect with each other. Therefore, contraction force F3 of the contraction force intersecting region 180 acts inward in a direction crossing the diaper longitudinal direction Y and the diaper transverse direction X.

The contraction force intersecting region 180 includes a first contraction force intersecting region 181 formed toward the abdomen-side end 110A of the disposable pet diaper 100 and a second contraction force intersecting region 182 formed toward the back-side end 130A.

As a result, as shown in FIG. 11, a first curved part 540 is formed in the abdomen-side end 110A and the back-side end 130A of the disposable pet diaper 100 and bulges outward in a direction from the inside surface 100Z1 to the outside surface 100Z2 of the disposable pet diaper 100 by the contraction force F2 of the waist stretchable elastic member 500.

The first curved part 540 includes a first abdomen-side curved part 541 formed in the abdomen-side end 110A of the disposable pet diaper 100 and a first back-side curved part 542 formed in the back-side end 130A.

Further, a second curved part 183 is formed in the contraction force intersecting region 180 and curved in the direction of the inside surface 100Z1 of the disposable pet diaper 100 by the contraction force F3 acting on the contraction force intersecting region 180.

The second curved part 183 includes a second abdomen-side curved part 184 formed in the first contraction force intersecting region 181 and a second back-side curved part 185 formed in the second contraction force intersecting region 182.

Figure 12:
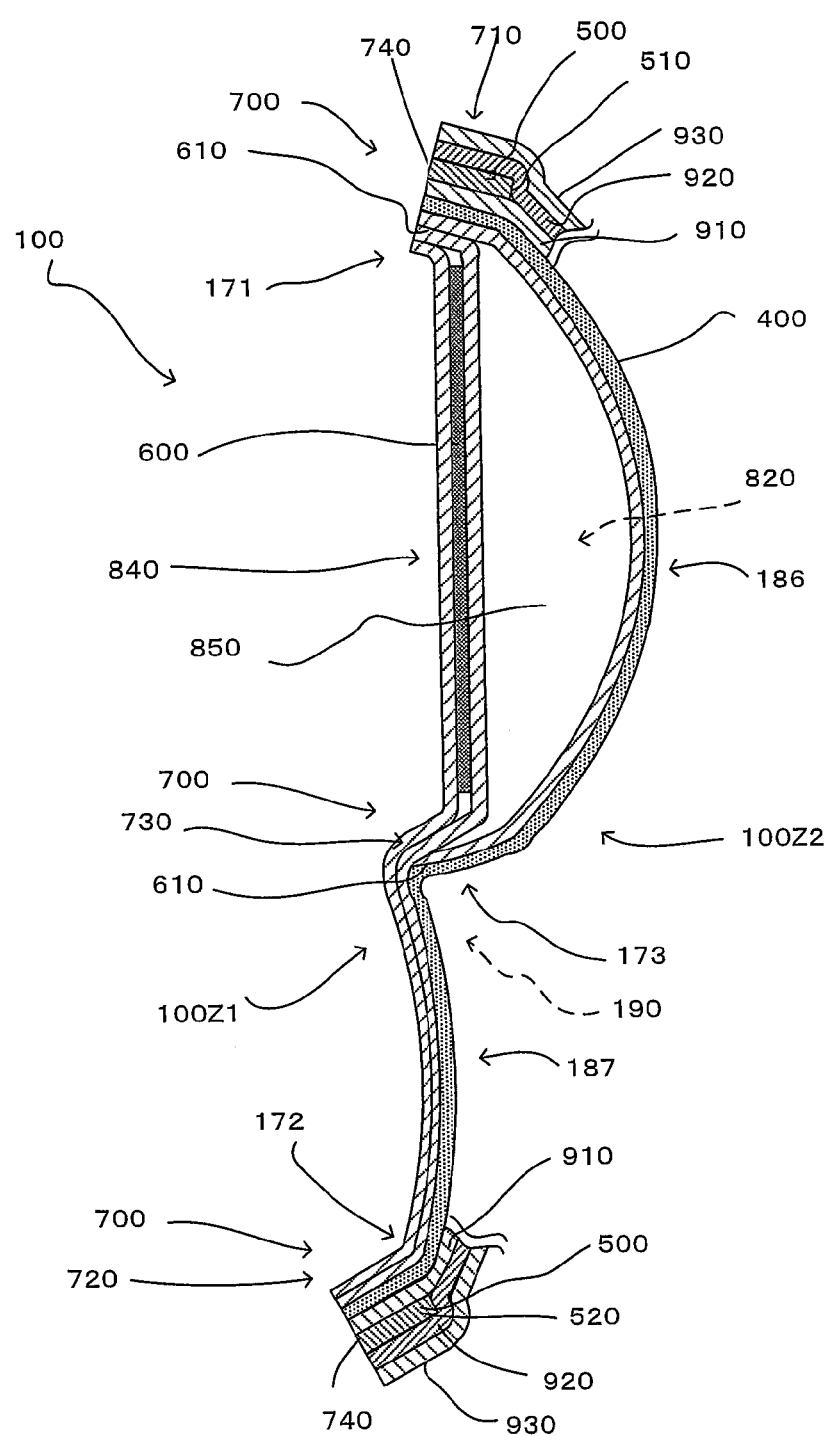
FIG. 12 is an explanatory drawing in a sectional view taken along line D-D in FIG. 1.

Now, the state in which the leg stretchable elastic member 400 and the leakproof sheet stretchable elastic member 600 are contracted is described with reference to FIG. 12. FIG. 12 is a sectional view taken along line D-D in FIG. 1, but, for convenience of explanation, part of the liquid-permeable sheet 910, the liquid-resistant sheet 920 and the outer sheet 930 and the whole of the absorbent core 200 and the fastening region 900 are not shown.

In FIG. 12, the leg stretchable elastic member 400 and the leakproof sheet stretchable elastic member 600 are contracted. As a result, the erected section 700 is formed by the contraction forces of the leg stretchable elastic member 400 and the leakproof sheet stretchable elastic member 600. Specifically, each of the abdomen-side erected region 171, the back-side erected region 172 and the crotch-side erected region 173 in the absorbent-core non-arrangement region 170 is erected and forms the erected section 700.

The erected section 700 includes an abdomen-side erected section 710, a back-side erected section 720 and a crotch-side erected section 730.

In this invention, as used herein, the term "erect" to form the erected section 700 means that the absorbent-core non-arrangement region 170 deforms by the contraction force of one of the stretchable elastic members or by a combination of the contraction forces of two or more of the stretchable elastic members.

The abdomen-side erected region 171 is erected by contraction of the leg stretchable elastic member 400 and forms the abdomen-side erected section 710.

The end of the leg stretchable elastic member 400 is arranged closer to the abdomen-side end 110A of the disposable pet diaper 100 than the end of the leakproof sheet stretchable elastic member 600. Therefore, the abdomen-side erected section 710 more strongly receives the influence of the contraction force of the leg stretchable elastic member 400 than the influence of the contraction force of the leakproof sheet stretchable elastic member 600. Specifically, the abdomen-side fixing part 620 of the contraction force fixing part 610 is moved by the contraction force of the leakproof sheet stretchable elastic member 600, which causes erection of the abdomen-side erected region 171. Therefore, the leakproof sheet stretchable elastic member 600 also forms the abdomen-side erected section 710.

The back-side erected region 172 is erected by contraction of the leg stretchable elastic member 400 and forms the back-side erected section 720.

The leg stretchable elastic member 400 is overlapped with the waist stretchable elastic member 500. Specifically, the both ends of the leg stretchable elastic member 400 are overlapped with the abdomen-side waist stretchable elastic member 510 and the back-side waist stretchable elastic member 520.

The waist stretchable elastic member 500 is arranged having a prescribed length in the diaper transverse direction. Therefore, the abdomen-side erected section 710 and the back-side erected section 720 erect the abdomen-side waist stretchable elastic member 510 and the back-side waist stretchable elastic member 520, respectively. Thus, the abdomen-side erected region 171 and the back-side erected region 172 are held in the stable erected state. Specifically, the abdomen-side waist stretchable elastic member 510 and the back-side waist stretchable elastic member 520 are provided as an erection sheet 740 to ensure the erected state of the erected section 700.

When the back-side fixing part 630 of the contraction force fixing part 610 is moved by contraction of the leakproof sheet stretchable elastic member 600, the crotch-side erected region 173 is erected and forms the crotch-side erected section 730.

Further, as described above, the leakproof wall 820 is formed by contraction of the leakproof sheet stretchable elastic member 600. A space surrounded by the leakproof wall 820, the abdomen-side erected section 710, the crotch-side erected section 730 and the absorbent core (not shown in FIG. 12) forms an excrement storage space 850.

A third curved part 640 is formed in a region extending from the abdomen-side end 110A to the tail insertion opening 190 in the disposable pet diaper 100 and bulges in a direction from the inside surface 100Z1 to the outside surface 100Z2 of the disposable pet diaper 100 by the contraction force F1 of the leg stretchable elastic member 400 and the leakproof sheet stretchable elastic member 600.

A fourth curved part 420 is formed in a region extending from the tail insertion opening 190 to the back-side end 130A in the disposable pet diaper 100 and bulges in a direction from the inside surface 100Z1 to the outside surface 100Z2 of the disposable pet diaper 100 mainly by the contraction force F1 of the leg stretchable elastic member 400.

Figure 13:
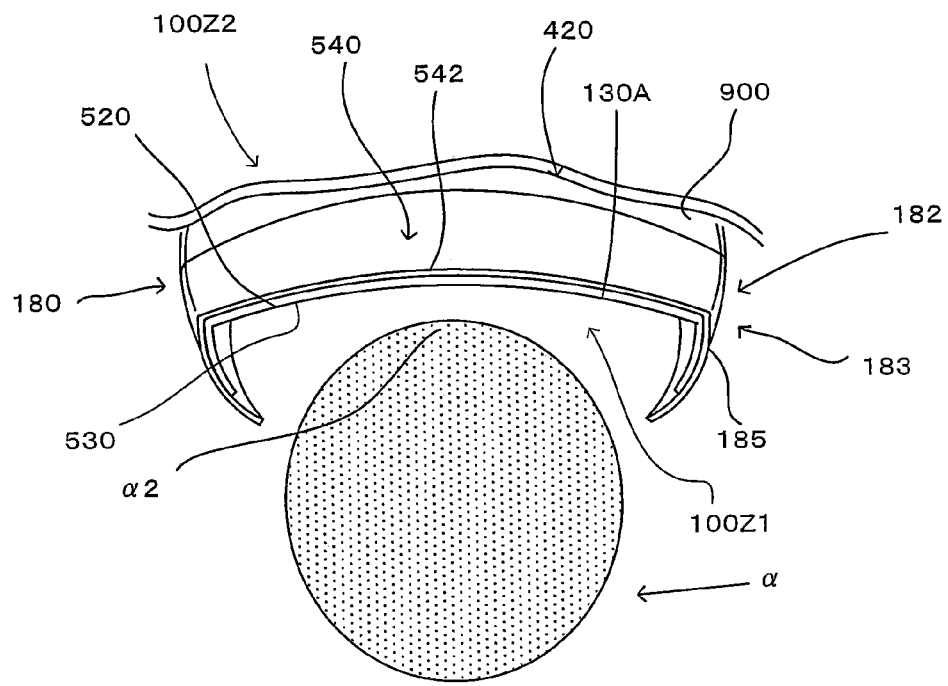
FIG. 13 is an explanatory drawing regarding to a back-side waist area in putting the disposable diaper on a pet.
Figure 14:
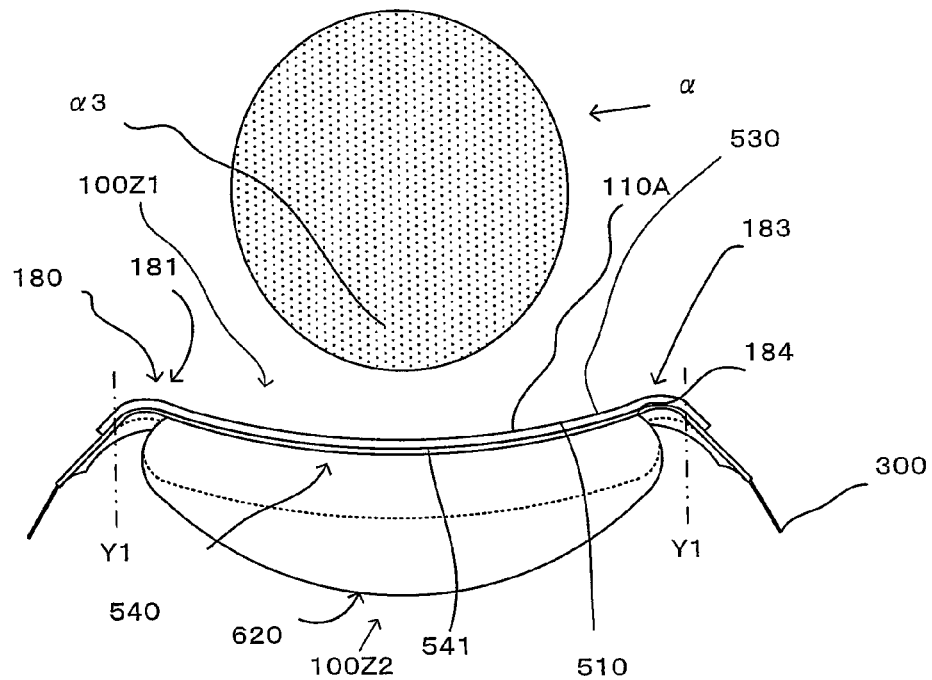
FIG. 14 is an explanatory drawing regarding to an abdomen-side waist area in putting the disposable diaper on a pet.

Next, putting the disposable pet diaper 100 on a pet is explained with reference to FIGS. 13 to 15. First, a user takes the disposable pet diaper 100 out of a package. In most cases, in the package, the abdomen-side flaps 150 and the back-side flaps 160 of the disposable pet diaper 100 are folded inward, and the disposable pet diaper 100 itself is folded, for example, into two or three.

When using the disposable pet diaper 100, the user unfolds the folded structure. At this time, the leg stretchable elastic member 400, the waist stretchable elastic member 500 and the leakproof sheet stretchable elastic member 600 contract. As a result, the erected section 700 including the abdomen-side erected section 710, the back-side erected section 720 and the crotch-side erected section 730 is formed, and the leakproof wall 820 is formed. Further, the first curved part 540, the second curved part 183, the third curved part 640 and the fourth curved part 420 are formed, and the leg gathers 410, the waist gathers 530 and the leakproof gathers 840 are formed. The shape of the disposable pet diaper 100 is stabilized by contraction of the leg stretchable elastic member 400, the waist stretchable elastic member 500 and the leakproof sheet stretchable elastic member 600.

Next, the user inserts the tail of the pet α through the tail insertion opening 190 of the disposable pet diaper 100.

Then the user covers the crotch and the abdomen of the pet α with the crotch area 120 and the abdomen-side waist area 110, with the back-side waist area 130 fitted closely to the back of the pet α. Then the free end 310 of the fastening part 300 is fastened to the fastening region 900. Thus, the disposable pet diaper 100 is put on the pet α.

These matters related to putting the disposable pet diaper 100 on the pet α is an example embodiment that corresponds to the feature that "when the disposable diaper is put on the pet, the crotch area and the abdomen-side waist area cover a crotch and an abdomen of the pet, while the back-side waist area is closely fitted to a back of the pet, and the fastening part is fastened to the fastening region" according to this invention.

The state of the disposable pet diaper 100 in fitting the back-side waist area 130 to the back of the pet α is explained with reference to FIG. 13.

The first curved part 540 bulging outward in the direction of the diaper outside surface 100Z2 is already formed in the back-side end 130A. Further, a region extending from the back-side end 130A to the tail insertion opening 190 is maintained in a stable shape by the fourth curved part 420. The back-side flap 160 is curved in the direction of the inside surface 100Z1 of the disposable pet diaper 100 together with the second contraction force intersecting region 182 by the second curved part 183.

Thus, the user can easily place the back-side end 130A along a curve of the back of the pet α.

Further, the back-side end 130A has a low possibility of being turned up.

The state of the disposable pet diaper 100 in covering the crotch and the abdomen of the pet α with the crotch area 120 and the abdomen-side waist area 110 and fastening the free end 310 of the fastening part 300 to the fastening region 900, is explained with reference to FIG. 14.

The first curved part 540 bulging in the direction of the diaper outside surface 100Z2 is already formed in the abdomen-side end 110A. Further, a region extending from the abdomen-side end 110A to the tail insertion opening 190 is maintained in a stable shape by the third curved part 640.

The abdomen-side flap 150 is curved together with the first contraction force intersecting region 181 in the direction of the inside surface 100Z1 of the disposable pet diaper 100 by the second curved part 183. In the abdomen-side flap 150 having the fastening part 300, the transverse end 150A is heavier than a boundary part of the abdomen-side flap 150 with the body 140B. Therefore, the boundary part of the abdomen-side flap 150 with the body 140B is curved in the direction of the inside surface 100Z1 together with the second curved part 183, while the transverse end 150A of the abdomen-side flap 150 is curved in the direction of the outside surface 100Z2 by its own weight. As a result, the fastening part 300 is supported on the abdomen-side flap 150 without hanging straight down.

Thus, the user can easily set the abdomen-side end 110A onto a curve of the abdomen of the pet α.

Further, the abdomen-side end 110A has a low possibility of being turned up.

Further, the user can easily grab the fastening part 300.

Furthermore, when the user moves the fastening part 300 toward the fastening region 900, the fastening part 300 receives the influence of the first contraction force intersecting region 181. Therefore, wherever the user moves the fastening part 300, the contraction force acts upon the fastening part 300. As a result, the user can easily move the fastening part 300 onto a desired position of the fastening region 900.

Figure 15:
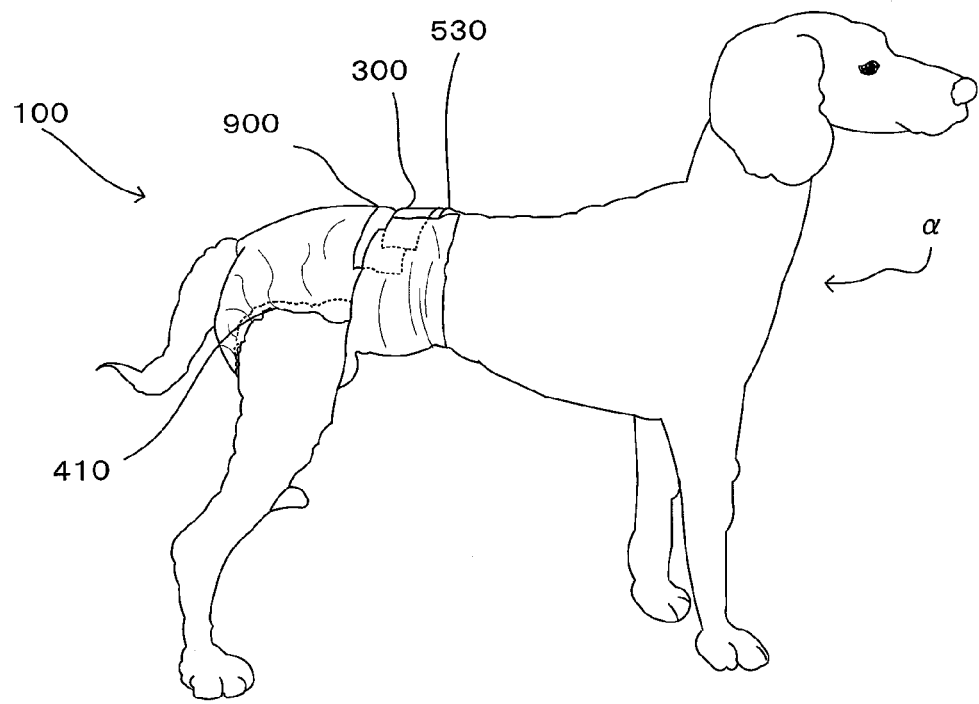
FIG. 15 is an explanatory drawing for illustrating the state of the disposable diaper worn by a pet.

FIG. 15 is a drawing for illustrating the state of the disposable pet diaper 100 worn by the pet α.

Even after the disposable pet diaper 100 has been put on the pet, the leg stretchable elastic member 400, the waist stretchable elastic member 500 and the leakproof sheet stretchable elastic member 600 are maintained in the contracted state. Therefore, the erected section 700 including the abdomen-side erected section 710, the back-side erected section 720 and the crotch-side erected section 730 is maintained in the erected state. The leakproof wall 820 is also maintained. Further, the first curved part 540, the second curved part 183, the third curved part 640 and the fourth curved part 420 are maintained in the curved state. The leg gathers 410, the waist gathers 530 and the leakproof gathers 840 are maintained.

When the pet α excretes, excrement is held within the excrement storage space 850. When the excrement is urine, it is absorbed by the absorbent core 200. When the excrement is feces, part of feces is absorbed by the absorbent core 200 and the rest is held within the excrement storage space 850.

Whether the excrement is urine or feces, the weight of the absorbent core 200 is received in the fastening part longitudinal direction 300X in the free part 310 of the fastening part 300.

This is an example embodiment that corresponds to the feature that "the weight of the absorbent core after excretion is received in the longitudinal direction of the fastening part while the disposable diaper is worn by the pet" according to this invention.

In order to remove the disposable pet diaper 100 from the pet α, the fastening part 300 is detached from the fastening region 900, and then the disposable pet diaper 100 is pulled off through the tail insertion opening 190 and disposed of.

In the process of detaching the fastening part 300 from the fastening region 900 and pulling off the disposable pet diaper 100 through the tail insertion opening 190, the abdomen-side end 110A is turned obliquely downward from the pet α. Even at this time, the risk of falling of feces can be reduced by the abdomen-side erected section 710.

Second to tenth embodiments of the present invention are now described with reference to FIGS. 16 to 24. In the description of the second to tenth embodiments, components which are identical to those in the first embodiment are not described in detail and their reference numerals are omitted.

Second Embodiment

Figure 16:
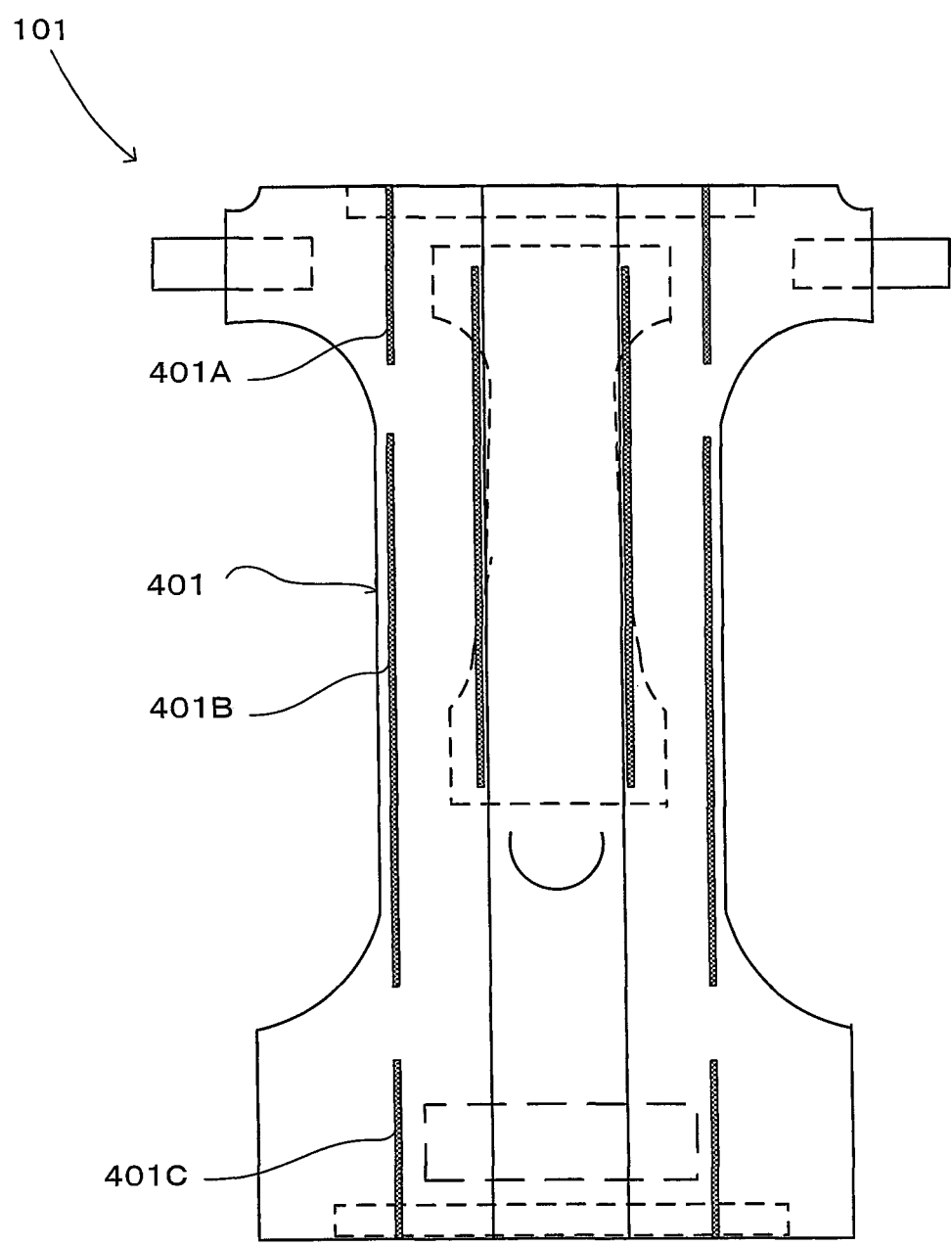
FIG. 16 is a plan view showing a disposable diaper for pets in its unfolded state according to a second embodiment of the present invention.

The second embodiment of the present invention is explained with reference to FIG. 16. A disposable pet diaper 101 according to the second embodiment is different from the disposable pet diaper 100 of the first embodiment in that a leg stretchable elastic member 401 includes a plurality of leg stretchable elastic members. Specifically, the leg stretchable elastic member 401 of the second embodiment is configured by continuously arranging a plurality of leg stretchable elastic members with intervals in the diaper longitudinal direction. The number of the continuously arranged leg stretchable elastic members can be appropriately selected according to the disposable pet diaper to be realized.

In the second embodiment of this invention, the leg stretchable elastic member 401 extending continuously in the diaper longitudinal direction includes three leg stretchable elastic members, or a leg stretchable elastic member 401A in the abdomen-side waist area, a leg stretchable elastic member 401B in the crotch area, and a leg stretchable elastic member 401C in the back-side waist area.

Like in the first embodiment, in the second embodiment, the erected section 700 including the abdomen-side erected section 710, the back-side erected section 720 and the crotch-side erected section 730 is formed, and the leakproof wall 820 is formed. Further, the first curved part 540 including the first abdomen-side curved part 541 and the first back-side curved part 542, the second curved part 183 including the second abdomen-side curved part 184 and the second back-side curved part 185, the third curved part 640 and the fourth curved part 420 are formed. Further, the leg gathers 410, the waist gathers 530 and the leakproof gathers 840 are formed.

Therefore, the disposable pet diaper 101 according to the second embodiment has the same effect as the disposable pet diaper 100 of the first embodiment.

Furthermore, by provision of the leg stretchable elastic member 401 including the three leg stretchable elastic members, the stretching forces of the leg stretchable elastic members can be prevented from affecting each other. Therefore, for example, the back-side waist area is little affected by displacement (or slippage) of the abdomen-side waist area, if any, so that the leg stretchable elastic member 401 can be prevented from causing displacement as a whole.

Third Embodiment

Figure 17:
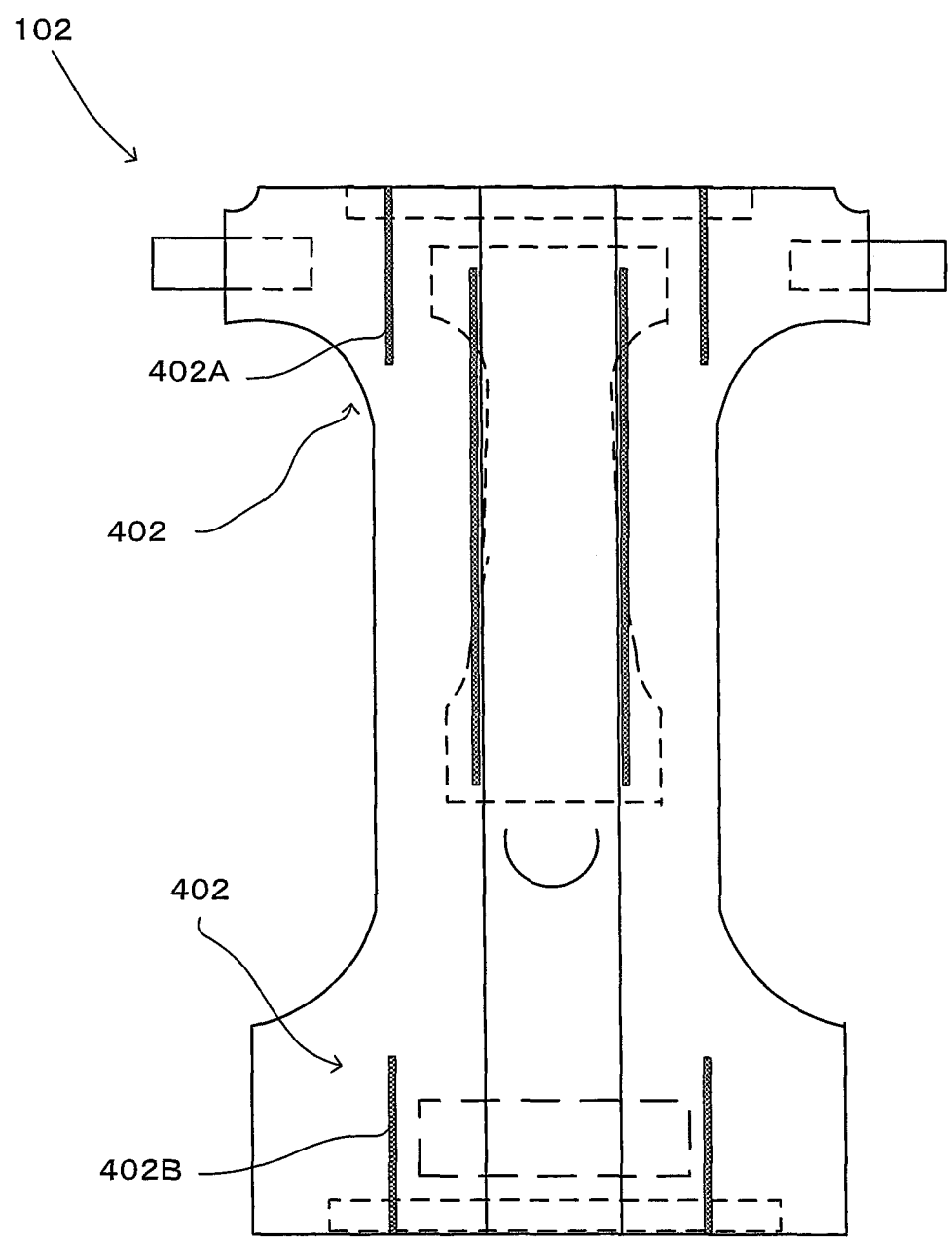
FIG. 17 is a plan view showing a disposable diaper for pets in its unfolded state according to a third embodiment of the present invention.

The third embodiment of the present invention is explained with reference to FIG. 17. A disposable pet diaper 102 according to the third embodiment is different from the disposable pet diaper 100 of the first embodiment in that a leg stretchable elastic member 402 is not continuously arranged in the diaper longitudinal direction.

Specifically, in the third embodiment of this invention, the leg stretchable elastic member 402 includes a leg stretchable elastic member 402A arranged in the abdomen-side waist area of the disposable pet diaper 102 and a leg stretchable elastic member 402B arranged in the back-side waist area.

The third embodiment is different from the first embodiment in that the leg gathers 410 and the fourth curved part 420 are formed only in the regions of the leg stretchable elastic members 402A and 402B in the disposable pet diaper 102.

In this structure, the erected section 700 including the abdomen-side erected section 710, the back-side erected section 720 and the crotch-side erected section 730 is formed, and the leakproof wall 820 is formed. Further, the first curved part 540 including the first abdomen-side curved part 541 and the first back-side curved part 542, the second curved part 183 including the second abdomen-side curved part 184 and the second back-side curved part 185, the third curved part 640 and part of the fourth curved part 420 are formed. Further, part of the leg gathers 410, the waist gathers 530 and the leakproof gathers 840 are formed.

Therefore, the disposable pet diaper 102 according to the third embodiment has all of the effects of the disposable pet diaper 100 of the first embodiment other than those exhibited by the whole leg gathers 410 and the whole fourth curved part 420.

Furthermore, in this structure, the stretchable elastic member is not provided in the crotch area in which the absorbent core is disposed, and nor in the free end of the leakproof gathers. Therefore, the absorbent core does not shrink, so that the area of the absorbent core can be effectively used.

Further, a pocket space can be readily formed in both end regions of the absorbent core in the diaper longitudinal direction.

Moreover, the stretchable elastic member is not provided in the fastening region. Therefore, the fastening region does not shrink, so that the fastening part can be easily engaged with the fastening region.

Fourth Embodiment

Figure 18:
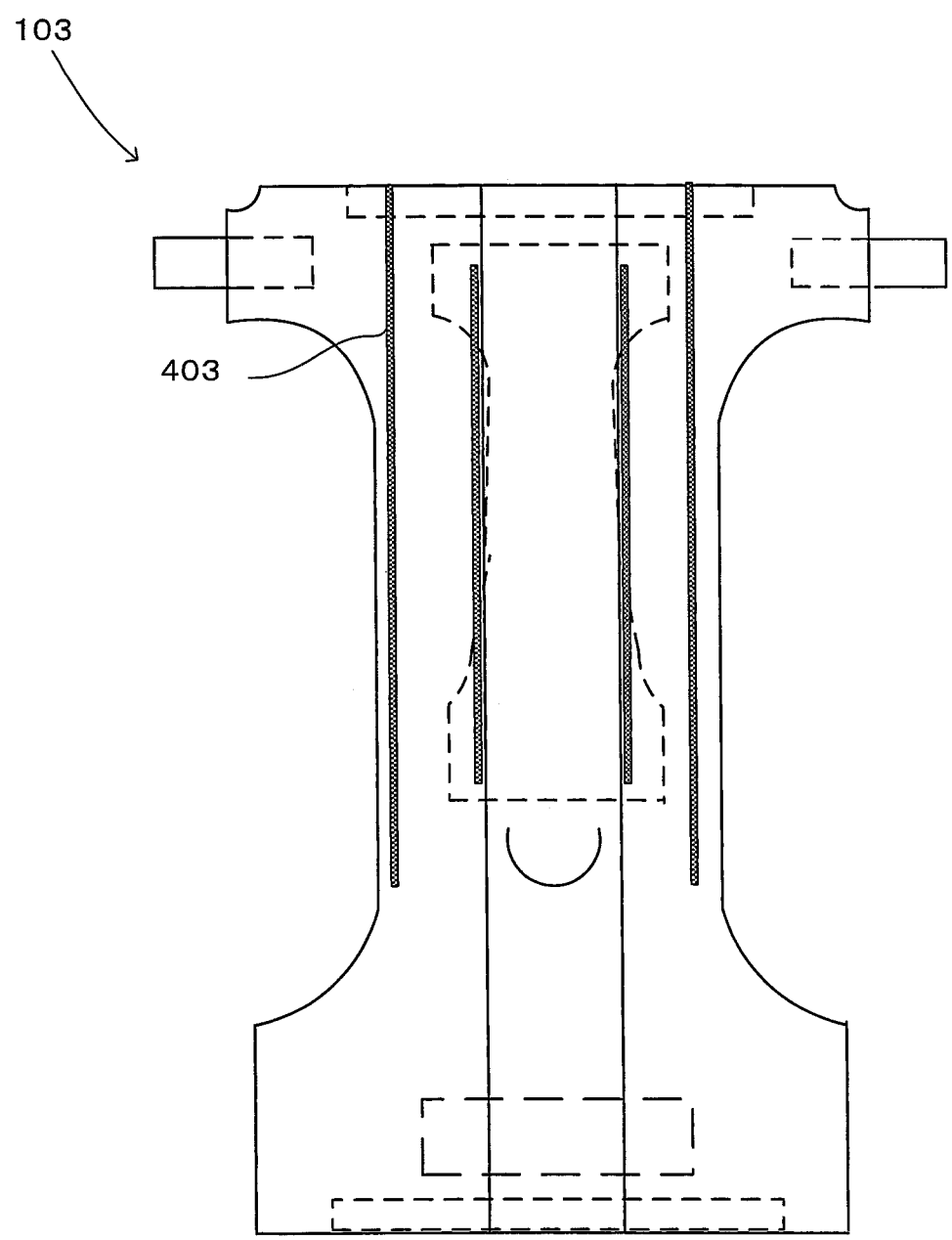
FIG. 18 is a plan view showing a disposable diaper for pets in its unfolded state according to a fourth embodiment of the present invention.

The fourth embodiment of the present invention is explained with reference to FIG. 18. A disposable pet diaper 103 according to the fourth embodiment is different from the disposable pet diaper 100 of the first embodiment in that a leg stretchable elastic member 403 is not provided in the back-side waist area. Further, the contraction force of the leakproof sheet stretchable elastic member exerts no influence on the abdomen-side end of the disposable pet diaper 103.

Compared with the disposable pet diaper 100 of the first embodiment, the disposable pet diaper 103 of the fourth embodiment is different in that the leg gathers 410 and the fourth curved part 420 are formed only in the region of the leg stretchable elastic member 403. Further, the back-side erected section 720 of the erected section 700 and the second back-side curved part 185 of the second curved part 183 are not formed.

In this structure, the erected section 700 including the abdomen-side erected section 710 and the crotch-side erected section 730 is formed, and the leakproof wall 820 is formed. Further, the first curved part 540 including the first abdomen-side curved part 541 and the first back-side curved part 542, the second curved part 183 including the second abdomen-side curved part 184, the third curved part 640 and part of the fourth curved part 420 are formed. Further, part of the leg gathers 410, the waist gathers 530 and the leakproof gathers 840 are formed.

Therefore, the disposable pet diaper 103 according to the fourth embodiment has all of the effects of the disposable pet diaper 100 of the first embodiment other than those exhibited by the whole leg gathers 410, the back-side erected section 720, the second back-side curved part 185 and the whole fourth curved part 420.

Further, a pocket space can be readily formed in back-side and abdomen-side end regions of the absorbent core.

Fifth Embodiment

Figure 19:
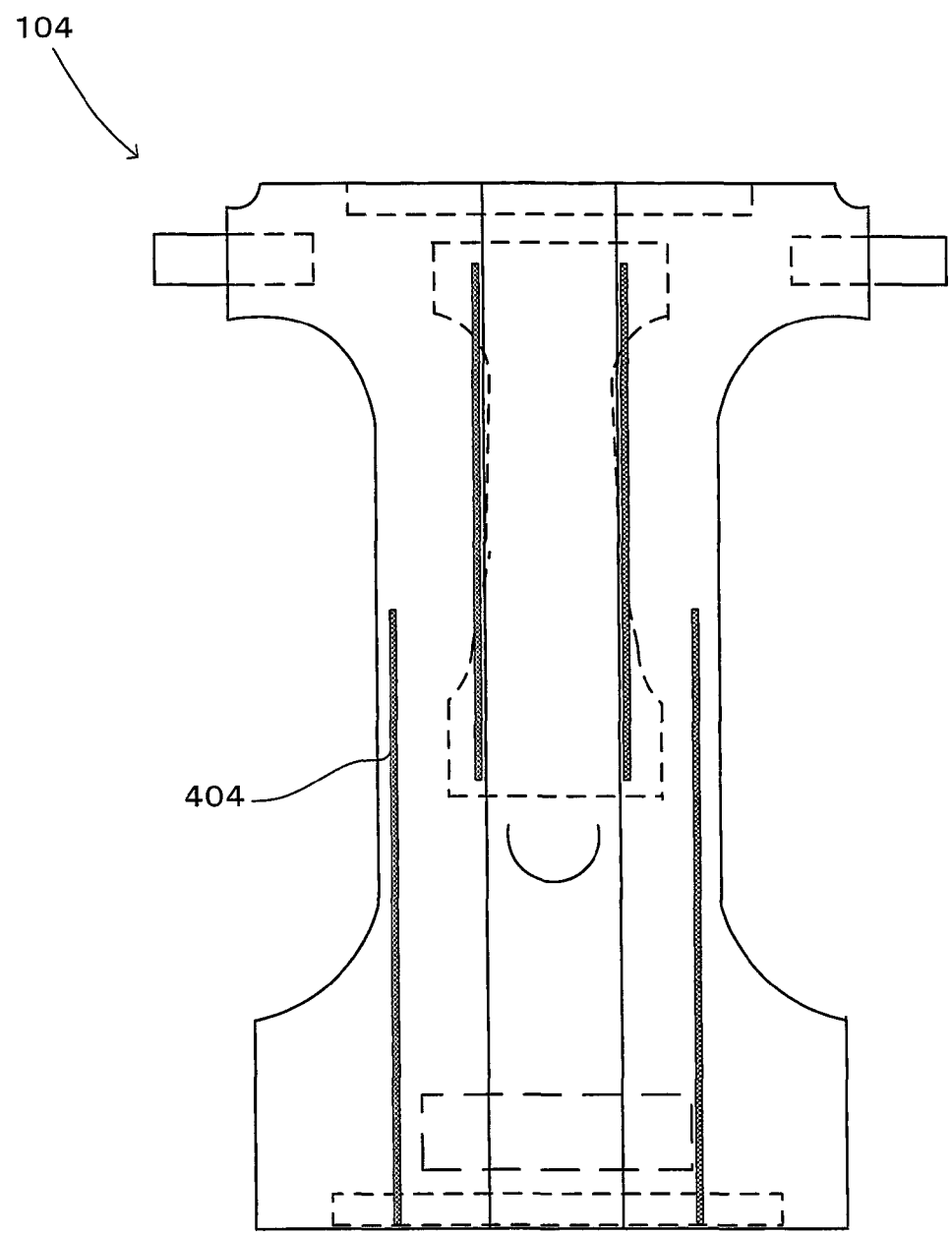
FIG. 19 is a plan view showing a disposable diaper for pets in its unfolded state according to a fifth embodiment of the present invention.

The fifth embodiment of the present invention is explained with reference to FIG. 19. A disposable pet diaper 104 according to the fifth embodiment is different from the disposable pet diaper 100 of the first embodiment in that a leg stretchable elastic member 404 is not provided in the abdomen-side waist area. Further, the contraction force of the leakproof sheet stretchable elastic member exerts no influence on the back-side end of the disposable pet diaper 104.

Compared with the disposable pet diaper 100 of the first embodiment, the disposable pet diaper 104 of the fifth embodiment is different in that the leg gathers 410 are formed only in the region of the leg stretchable elastic member 404. Further, the abdomen-side erected section 710 of the erected section 700 and the second abdomen-side curved part 184 of the second curved part 183 are not formed.

In this structure, the erected section 700 including the back-side erected section 720 and the crotch-side erected section 730 is formed, and the leakproof wall 820 is formed. Further, the first curved part 540 including the first abdomen-side curved part 541 and the first back-side curved part 542, the second curved part 183 including the second back-side curved part 185, the third curved part 640 and the fourth curved part 420 are formed. Further, part of the leg gathers 410, the waist gathers 530 and the leakproof gathers 840 are formed.

Therefore, the disposable pet diaper 104 according to the fifth embodiment has all of the effects of the disposable pet diaper 100 of the first embodiment other than those exhibited by the whole leg gathers 410, the abdomen-side erected section 710 and the second abdomen-side curved part 184.

Further, the absorbent core is not subjected to a contraction force, so that the area of the absorbent core can be effectively used.

Moreover, by provision of the leg stretchable elastic member only in the back-side area, it is made easier to fit the disposable pet diaper along the back of the pet. As a result, the fastening part can be easily engaged with the fastening region.

Sixth Embodiment

Figure 20:
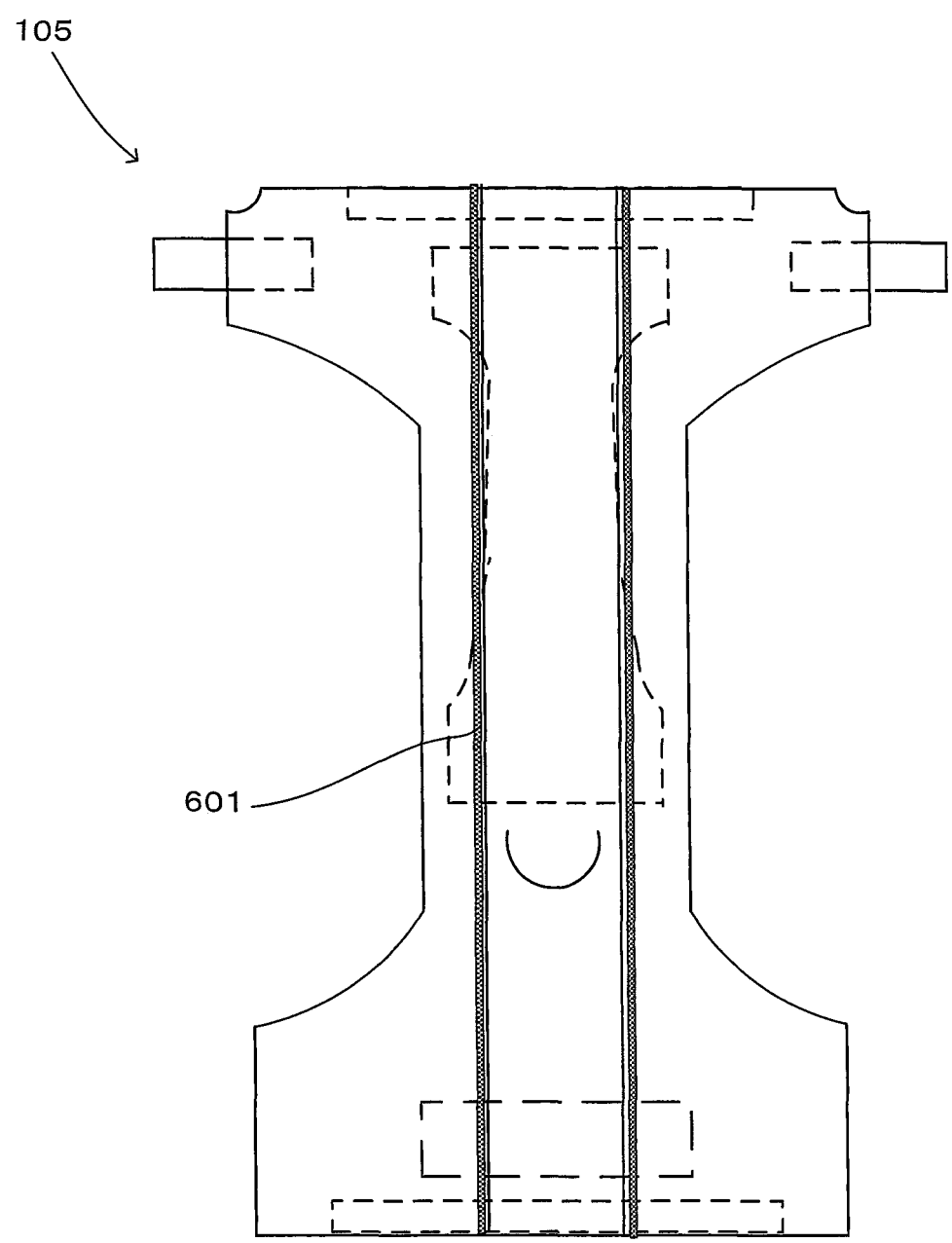
FIG. 20 is a plan view showing a disposable diaper for pets in its unfolded state according to a sixth embodiment of the present invention.

The sixth embodiment of the present invention is explained with reference to FIG. 20. A disposable pet diaper 105 according to the sixth embodiment is different from the disposable pet diaper 100 of the first embodiment in that a leg stretchable elastic member is not provided, and a leakproof sheet stretchable elastic member 601 is arranged to extend from the abdomen-side end to the back-side end of the disposable pet diaper 105. The abdomen-side fixing part and the back-side fixing part are formed on the abdomen-side end and the back-side end of the disposable pet diaper 105, respectively, in the fixed part of the leakproof sheet. The leakproof sheet stretchable elastic member 601 is overlapped with the abdomen-side waist stretchable elastic member and the back-side waist stretchable elastic member of the waist stretchable elastic member.

A comparison is made between the disposable pet diaper 100 of the first embodiment and the disposable pet diaper 105 of the sixth embodiment. In the disposable pet diaper 105 of the sixth embodiment, the erected section 700 including the abdomen-side erected section 710 and the back-side erected section 720, the leakproof wall 820, the leakproof gathers 840, the third curved part 640 and the fourth curved part 420 are formed by the action of the leakproof sheet stretchable elastic member 601.

The first abdomen-side curved part 541 and the first back-side curved part 542 are formed by the action of the waist stretchable elastic member, or by the actions of the abdomen-side waist stretchable elastic member and the back-side waist stretchable elastic member, respectively.

The first contraction force intersecting region 181 is formed by the contraction force of the leakproof sheet stretchable elastic member 601 and the contraction force of the abdomen-side waist stretchable elastic member. As a result, the second abdomen-side curved part 184 is formed.

Further, the second contraction force intersecting region 182 is formed by the leakproof sheet stretchable elastic member 601 and the contraction force of the back-side waist stretchable elastic member. As a result, the second back-side curved part 185 is formed.

Specifically, in the disposable pet diaper 105 of the sixth embodiment, unlike in the disposable pet diaper 100 of the first embodiment, the crotch-side erected section 730 and the leg gathers 410 are not formed.

Therefore, the disposable pet diaper 105 of the sixth embodiment has all of the effects of the disposable pet diaper 100 of the first embodiment other than those exhibited by the leg gathers 410 and the crotch-side erected section 730.

Furthermore, in the disposable pet diaper 105 of the sixth embodiment, due to the absence of the leg stretchable elastic member, the ends of the disposable pet diaper 105 in the diaper transverse direction can be located closer to the absorbent core. As a result, a portion of the disposable pet diaper 105 which comes in contact with the pet's legs can be further reduced.

Further, due to the absence of a sheet forming a portion around legs, the disposable pet diaper when worn can be made neat around legs.

Seventh Embodiment

Figure 21:
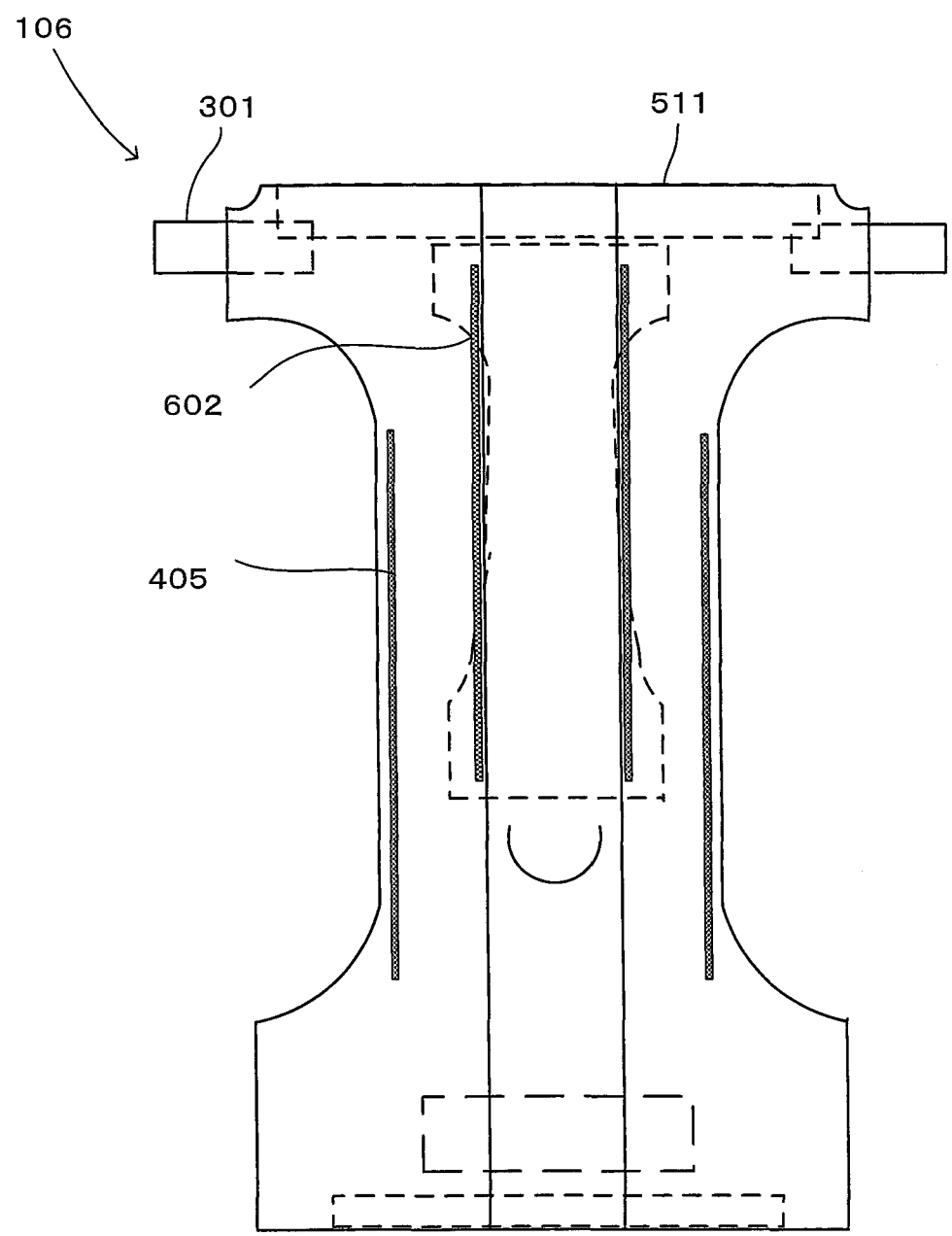
FIG. 21 is a plan view showing a disposable diaper for pets in its unfolded state according to a seventh embodiment of the present invention.

The seventh embodiment of the present invention is explained with reference to FIG. 21. A disposable pet diaper 106 according to the seventh embodiment is different from the disposable pet diaper 100 of the first embodiment in that a leg stretchable elastic member 404 is not provided in the abdomen-side waist area and the back-side waist area. Further, the contraction force of the leakproof sheet stretchable elastic member exerts no influence on the abdomen-side end of the disposable pet diaper 106. Further, an abdomen-side waist stretchable elastic member 511 is overlapped with fastening parts 301. The feature that "an abdomen-side waist stretchable elastic member is overlapped with fastening parts" according to this invention does not mean that the abdomen-side waist stretchable elastic member is in direct contact with the fastening parts. Specifically, it means that the contraction force of the abdomen-side waist stretchable elastic member does not act on the fastening parts via flaps, but it directly act on them.

A comparison is made between the disposable pet diaper 100 of the first embodiment and the disposable pet diaper 106 of the seventh embodiment. In the disposable pet diaper 106 of the seventh embodiment, the leg gathers 410 are formed only in a region of the leg stretchable elastic member 401. Further, the abdomen-side erected section 710 and the back-side erected section 720 of the erected section 700 are not formed. The second abdomen-side curved part 184 and the second back-side curved part 185 of the second curved part 183 are not formed. The fourth curved part 420 is formed only in the region of the leg stretchable elastic member 405.

In this structure, the erected section 700 including the crotch-side erected section 730 is formed, and the leakproof wall 820 is formed. Further, the first curved part 540 including the first abdomen-side curved part 541 and the first back-side curved part 542, the third curved part 640 and part of the fourth curved part 420 are formed. Part of the leg gathers 410 and the leakproof gathers 840 are formed.

Therefore, the disposable pet diaper 106 according to the seventh embodiment has those of the effects of the disposable pet diaper 100 of the first embodiment which are exhibited by the crotch-side erected section 730, the leakproof wall 820, the first abdomen-side curved part 541, the first back-side curved part 542, the third curved part 640, part of the fourth curved part 420, part of the leg gathers 410 and the leakproof gathers 840.

Furthermore, by provision of the abdomen-side waist stretchable elastic member 511 overlapped with the fastening parts 301, when the abdomen-side waist area is set on the abdomen of the pet in order to put the disposable pet diaper 106 on the pet, the fastening parts 301 are curved inside the disposable pet diaper under the influence of the contraction force of the abdomen-side waist stretchable elastic member 511. Thus, it is made easier for the user to grab the fastening parts 301.

Eighth Embodiment

Figure 22:
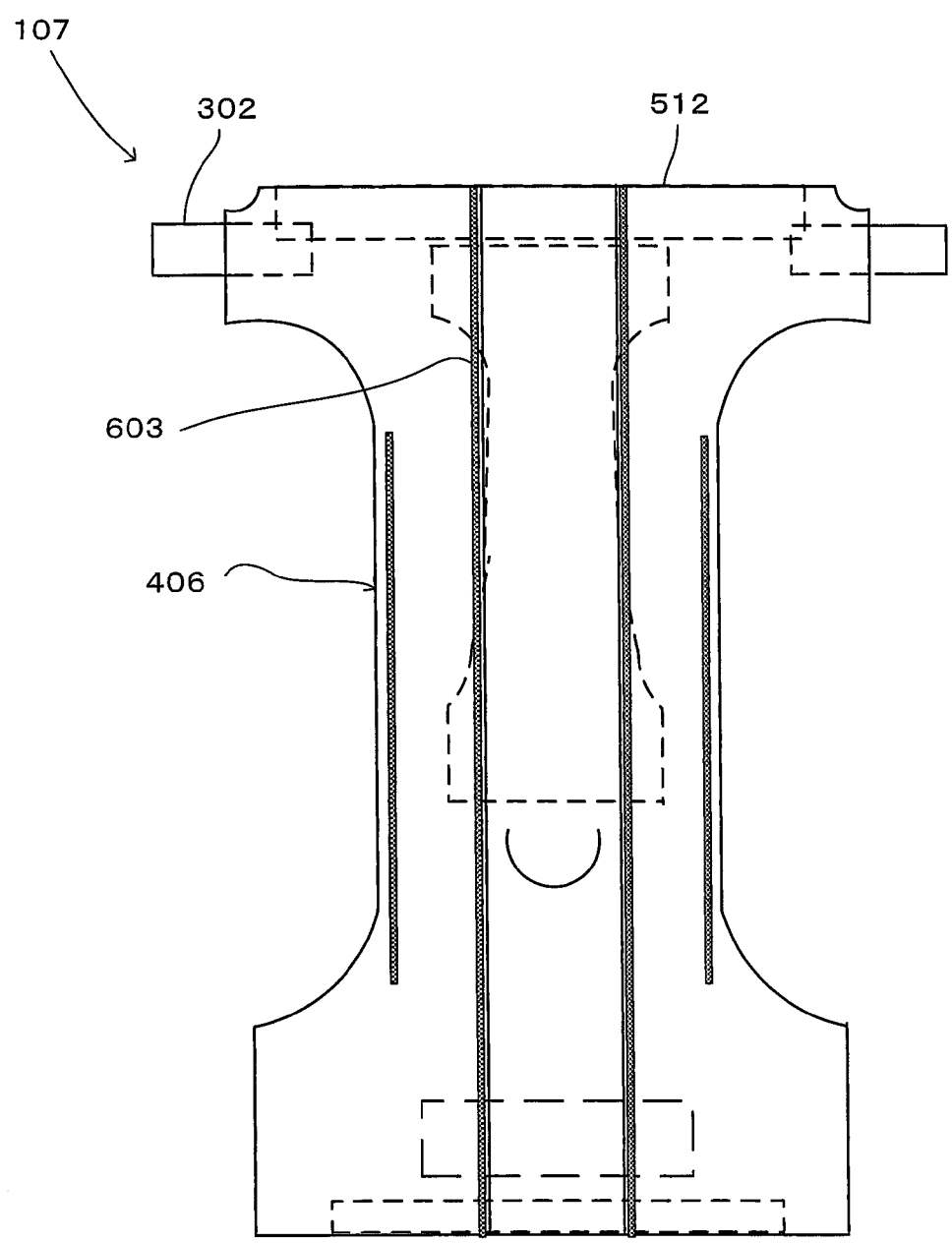
FIG. 22 is a plan view showing a disposable diaper for pets in its unfolded state according to an seventh embodiment of the present invention.

The eighth embodiment of the present invention is explained with reference to FIG. 22. A disposable pet diaper 107 according to the eighth embodiment is different from the disposable pet diaper 100 of the first embodiment in that a leg stretchable elastic member 406 is not provided in the abdomen-side waist area and the back-side waist area of the disposable pet diaper 107. Further, a leakproof sheet stretchable elastic member 603 is arranged to extend from the abdomen-side end to the back-side end of the disposable pet diaper 107. The abdomen-side fixing part and the back-side fixing part are formed on the abdomen-side end and the back-side end of the disposable pet diaper 107, respectively, in the fixed part of the leakproof sheet. The leakproof sheet stretchable elastic member 603 is overlapped with an abdomen-side waist stretchable elastic member 512 and the back-side waist stretchable elastic member of the waist stretchable elastic member. The abdomen-side waist stretchable elastic member 512 is overlapped with the fastening parts 302.

A comparison is made between the disposable pet diaper 100 of the first embodiment and the disposable pet diaper 107 of the eighth embodiment. In the disposable pet diaper 107 of the eighth embodiment, the erected section 700 including the abdomen-side erected section 710 and the back-side erected section 720, the leakproof wall 820, the leakproof gathers 840, the third curved part 640 and the fourth curved part 420 are formed by the action of the leakproof sheet stretchable elastic member 603.

The first abdomen-side curved part 541 and the first back-side curved part 542 are formed by the action of the waist stretchable elastic member, or by the actions of the abdomen-side waist stretchable elastic member 512 and the back-side waist stretchable elastic member, respectively.

The first contraction force intersecting region 181 is formed by the contraction force of the leakproof sheet stretchable elastic member 603 and the contraction force of the abdomen-side waist stretchable elastic member. As a result, the second abdomen-side curved part 184 is formed.

Further, the second contraction force intersecting region 182 is formed by the contraction force of the leakproof sheet stretchable elastic member 603 and the contraction force of the back-side waist stretchable elastic member. As a result, the second back-side curved part 185 is formed.

Specifically, in the disposable pet diaper 107 of the eighth embodiment, unlike in the disposable pet diaper 100 of the first embodiment, the crotch-side erected section 730 and part of the leg gathers 410 are not formed.

Therefore, the disposable pet diaper 107 of the eighth embodiment has all of the effects of the disposable pet diaper 100 of the first embodiment other than those exhibited by the whole leg gathers 410 and the crotch-side erected section 730.

Furthermore, due to the absence of the waist stretchable elastic member in the abdomen-side region and the back-side region, the abdomen-side region and the back-side region can be fitted around the waist of the pet while the fastening member is engaged.

Further, a pocket can be formed in both end regions of the absorbent core in the diaper longitudinal direction.

Furthermore, by provision of the abdomen-side waist stretchable elastic member 512 overlapped with the fastening parts 302, when the abdomen-side waist area is set on the abdomen of the pet in order to put the disposable pet diaper 107 on the pet, the fastening parts 302 are curved inside the disposable pet diaper under the influence of the contraction force of the abdomen-side waist stretchable elastic member 512. Thus, it is made easier for the user to grab the fastening parts 302.

Ninth Embodiment

Figure 23:
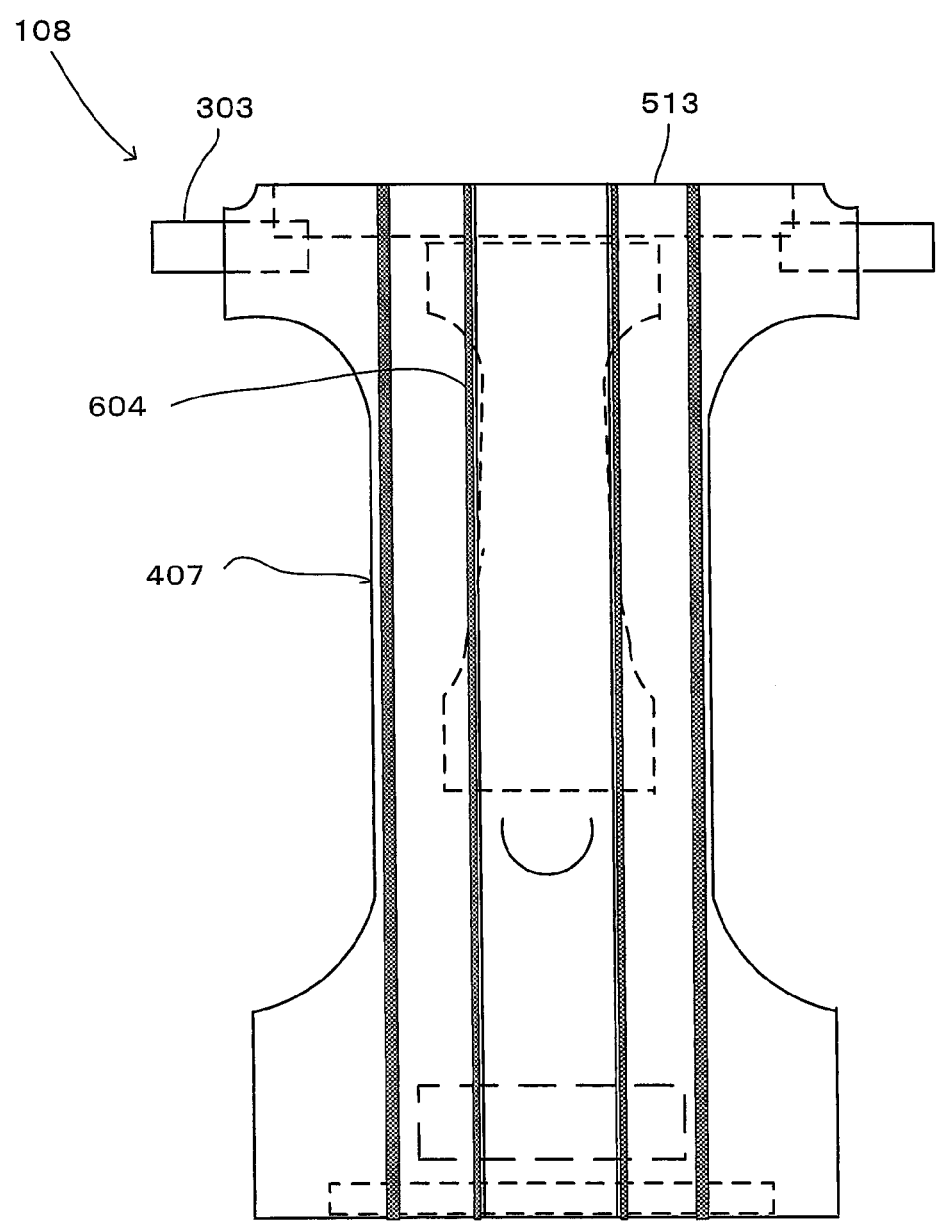
FIG. 23 is a plan view showing a disposable diaper for pets in its unfolded state according to a eighth embodiment of the present invention.

The ninth embodiment of the present invention is explained with reference to FIG. 23. A disposable pet diaper 108 according to the ninth embodiment is different from the disposable pet diaper 100 of the first embodiment in that a leakproof sheet stretchable elastic member 604 is arranged to extend from the abdomen-side end to the back-side end of the disposable pet diaper 108. The abdomen-side fixing part and the back-side fixing part are formed on the abdomen-side end and the back-side end of the disposable pet diaper 108, respectively, in the fixed part of the leakproof sheet. The leakproof sheet stretchable elastic member 604 is overlapped with an abdomen-side waist stretchable elastic member 513 and the back-side waist stretchable elastic member of the waist stretchable elastic member. Further, the abdomen-side waist stretchable elastic member 513 is overlapped with fastening parts 303.

A comparison is made between the disposable pet diaper 100 of the first embodiment and the disposable pet diaper 108 of the ninth embodiment. In the disposable pet diaper 108 of the ninth embodiment, the erected section 700 including the abdomen-side erected section 710 and the back-side erected section 720, the leg gathers 410, the leakproof wall 820, the leakproof gathers 840, the third curved part 640 and the fourth curved part 420 are formed by the actions of a leg stretchable elastic member 407 and the leakproof sheet stretchable elastic member 604.

The first abdomen-side curved part 541 and the first back-side curved part 542 are formed by the action of the waist stretchable elastic member, or by the actions of the abdomen-side waist stretchable elastic member 513 and the back-side waist stretchable elastic member, respectively.

Two structures of the first contraction force intersecting regions 181 are formed. One is formed by intersection of the contraction forces of the leg stretchable elastic member 407 and the abdomen-side waist stretchable elastic member 513, and the other is formed by the contraction force of the leakproof sheet stretchable elastic member 604 and the contraction force of the abdomen-side waist stretchable elastic member 513. Accordingly, two structures of the second abdomen-side curved parts 184 are formed by formation of the two first contraction force intersecting regions 181.

Similarly, two structures of the second contraction force intersecting regions 182 are formed. One is formed by intersection of the contraction forces of the leg stretchable elastic member 407 and the back-side waist stretchable elastic member, and the other is formed by the contraction force of the leakproof sheet stretchable elastic member 604 and the contraction force of the back-side waist stretchable elastic member. Accordingly, two structures of the second back-side curved parts 185 are formed by formation of the two second contraction force intersecting regions 182.

Specifically, unlike in the disposable pet diaper 100 of the first embodiment, the crotch-side erected section 730 is not formed in the disposable pet diaper 108 of the ninth embodiment.

Therefore, the disposable pet diaper 108 of the ninth embodiment has all of the effects of the disposable pet diaper 100 of the first embodiment other than those exhibited by the crotch-side erected section 730.

Furthermore, by provision of the abdomen-side waist stretchable elastic member 513 overlapped with the fastening parts 303, when the abdomen-side waist area is set on the abdomen of the pet in order to put the disposable pet diaper 108 on the pet, the fastening parts 303 are curved inside the disposable pet diaper under the influence of the contraction force of the abdomen-side waist stretchable elastic member 513. Thus, it is made easier for the user to grab the fastening parts 303.

Further, the contraction forces act over the whole diaper in the diaper longitudinal direction, so that leakage of excrement can be prevented. Therefore, this disposable pet diaper is particularly suitable for bedridden pets.

Tenth Embodiment

Figure 24:
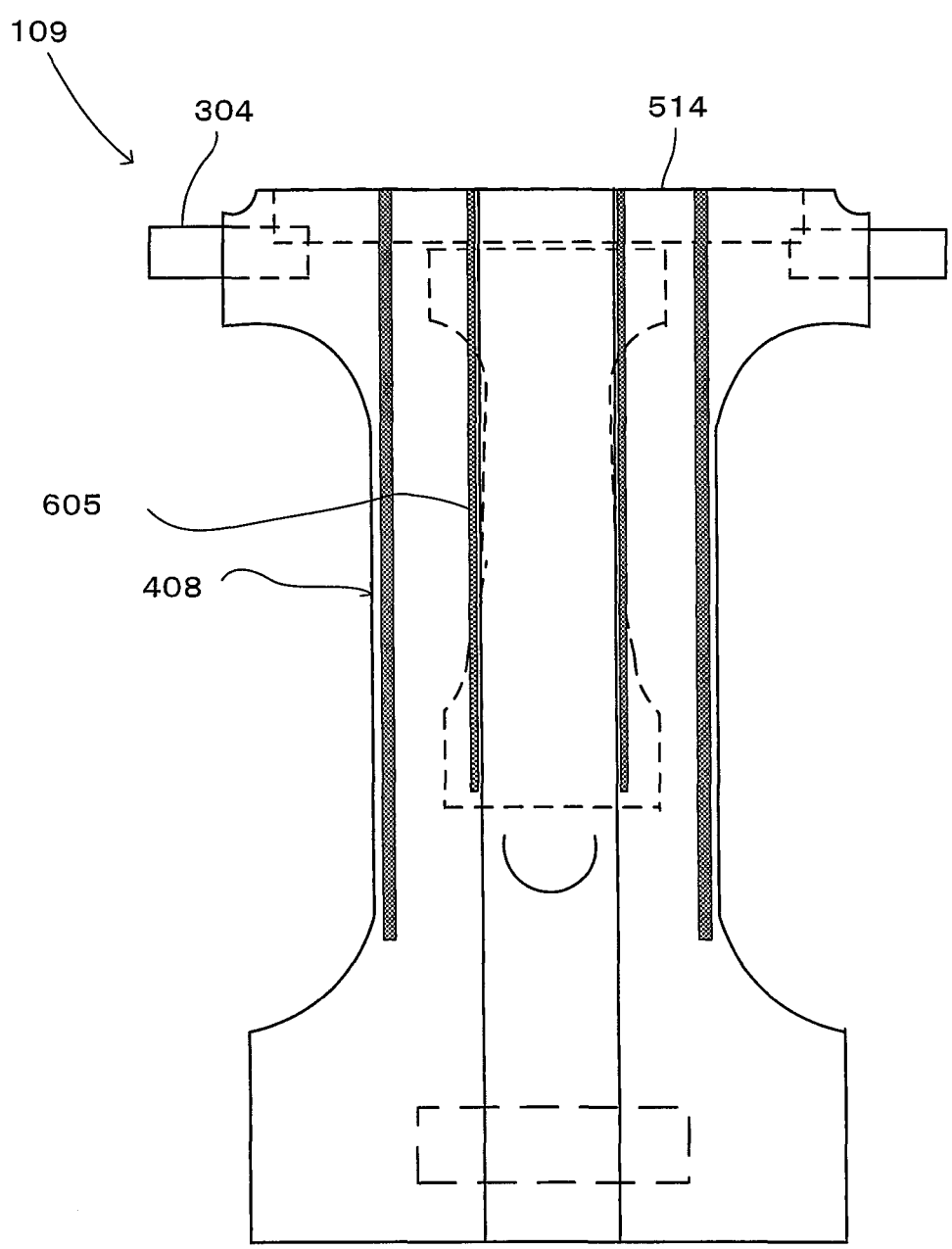
FIG. 24 is a plan view showing a disposable diaper for pets in its unfolded state according to a ninth embodiment of the present invention.
Figure 25:
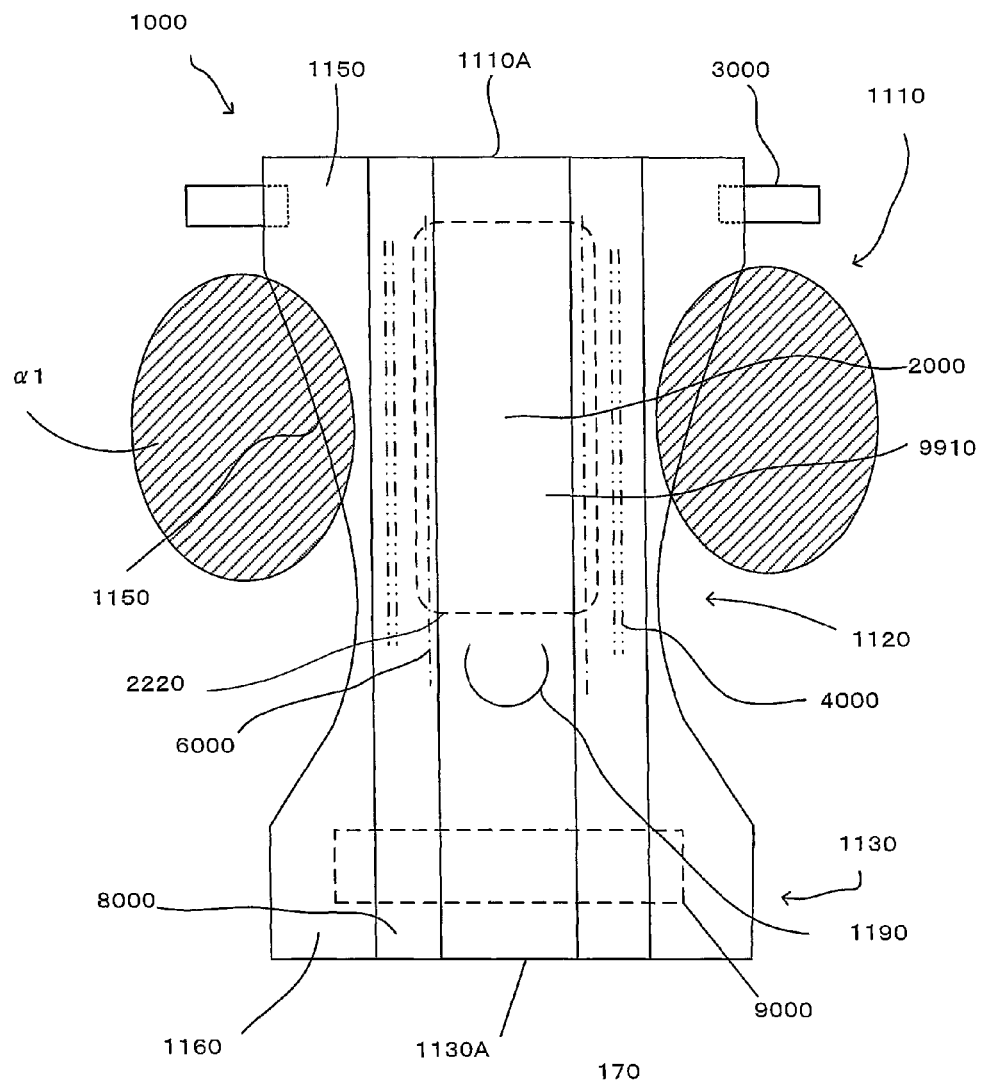
FIG. 25 is a plan view showing a prior art disposable diaper for pets in its unfolded state.
Figure 26:
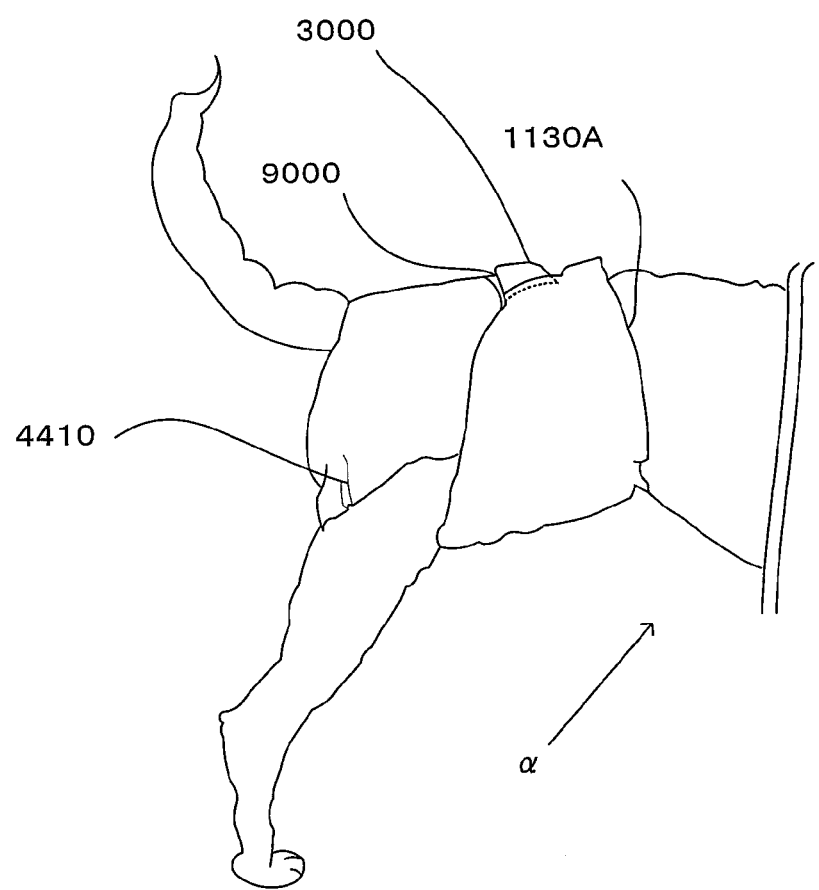
FIG. 26 is an explanatory drawing for illustrating a state of the prior art disposable diaper worn by a pet.

The tenth embodiment of the present invention is explained with reference to FIG. 24. A disposable pet diaper 109 according to the tenth embodiment is different from the disposable pet diaper 100 of the first embodiment in that a leg stretchable elastic member 408 is not provided in the back-side waist area. Further, a leakproof sheet stretchable elastic member 605 is arranged to extend up to the abdomen-side end of the disposable pet diaper 109. The abdomen-side fixing part is formed on the abdomen-side end of the disposable pet diaper 109 in the fixed part of the leakproof sheet. The leakproof sheet stretchable elastic member 602 is overlapped with an abdomen-side waist stretchable elastic member 514 of the waist stretchable elastic member. Further, the abdomen-side waist stretchable elastic member 514 is overlapped with fastening parts 304.

A comparison is made between the disposable pet diaper 100 of the first embodiment and the disposable pet diaper 109 of the tenth embodiment. In the disposable pet diaper 109 of the tenth embodiment, the erected section 700 including the abdomen-side erected section 710 and the crotch-side erected section 730, part of the leg gathers 410, the leakproof wall 820, the leakproof gathers 840, the third curved part 640 and part of the fourth curved part 420 are formed by the actions of the leg stretchable elastic member 408 and the leakproof sheet stretchable elastic member 605.

The first abdomen-side curved part 541 is formed by the action of the waist stretchable elastic member or the abdomen-side waist stretchable elastic member 514.

Two structures of the first contraction force intersecting regions 181 are formed. One is formed by intersection of the contraction forces of the leg stretchable elastic member 408 and the abdomen-side waist stretchable elastic member 514, and the other is formed by the contraction force of the leakproof sheet stretchable elastic member 605 and the contraction force of the abdomen-side waist stretchable elastic member 514. Accordingly, two structures of the second abdomen-side curved parts 184 are formed by formation of the two first contraction force intersecting regions 181.

Specifically, unlike in the disposable pet diaper 100 of the first embodiment, the back-side erected section 720, part of the leg gathers 410, the first back-side curved part 542, the second back-side curved part 185 and part of the fourth curved part 420 are not formed in the disposable pet diaper 109 of the tenth embodiment.

Therefore, the disposable pet diaper 109 of the tenth embodiment has all of the effects of the disposable pet diaper 100 of the first embodiment other than those exhibited by the back-side erected section 720, the whole leg gathers 410, the first back-side curved part 542, the second back-side curved part 185 and the whole fourth curved part 420.

In this structure, the contraction forces strongly act only on the abdomen-side region, so that a pocket can be readily formed in an abdomen-side region of the absorbent core. Therefore, this disposable pet diaper is suitable as a disposable diaper for male pets.

Furthermore, by provision of the abdomen-side waist stretchable elastic member 514 overlapped with the fastening parts 304, when the abdomen-side waist area is set on the abdomen of the pet in order to put the disposable pet diaper 109 on the pet, the fastening parts 304 are curved inside the disposable pet diaper under the influence of the contraction force of the abdomen-side waist stretchable elastic member 514. Thus, it is made easier for the user to grab the fastening parts 304.

The structures or features of the disposable pet diaper according to this invention are not limited to those described above. The structures or features of the first to tenth embodiments can be appropriately used in combination.
(Correspondences Between the Features of the Embodiments and the Features of the Invention)

The disposable pet diaper 100, 101, 102, 103, 104, 105, 106, 107, 108, 109 is an example embodiment that corresponds to the "disposable diaper for pets" according to this invention. The back-side waist area 130 is an example embodiment that corresponds to the "back-side waist area" according to this invention. The abdomen-side waist area 110 is an example embodiment that corresponds to the "abdomen-side waist area" according to this invention. The crotch area 120 is an example embodiment that corresponds to the "crotch area" according to this invention. The abdomen-side flap 150 is an example embodiment that corresponds to the "flap" according to this invention. The diaper longitudinal direction Y and the diaper transverse direction X are example embodiments that correspond to the "diaper longitudinal direction" and the "diaper transverse direction", respectively, according to this invention. The ends 110A and 130A are an example embodiment that corresponds to the "both ends in the diaper longitudinal direction" according to this invention. The ends 100A are an example embodiment that corresponds to the "both ends in the diaper transverse direction" according to this invention. The diaper longitudinal center line 100Y2 is an example embodiment that corresponds to the "diaper longitudinal center line" according to this invention. The diaper center point 100P is an example embodiment that corresponds to the "diaper center point" according to this invention. The tail insertion opening 190 is an example embodiment that corresponds to the "tail insertion opening" according to this invention. The absorbent core 200 is an example embodiment that corresponds to the "absorbent core" according to this invention. The fastening part 300, 301, 302, 303, 304 is an example embodiment that corresponds to the "fastening part" according to this invention. The fastening part longitudinal direction 300X is an example embodiment that corresponds to the "fastening part longitudinal direction" according to this invention. The fastening part transverse direction 300Y is an example embodiment that corresponds to the "fastening part transverse direction" according to this invention. The fastening part midpoint 300P1 is an example embodiment that corresponds to the "fastening part midpoint" according to this invention. The fastening region 900 is an example embodiment that corresponds to the "fastening region" according to this invention. The shortest line point 300P2 is an example embodiment that corresponds to the "shortest line point" according to this invention. The measured length D2 is an example embodiment that corresponds to the "straight-line distance between the shortest line point and a diaper end center point at which the end in the diaper longitudinal direction in the abdomen-side waist area and the diaper longitudinal center line intersect" according to this invention. The diaper longitudinal length D1 is an example embodiment that corresponds to the "straight-line distance between the abdomen-side end and the back-side end on the diaper longitudinal center line" according to this invention.

In view of the nature of the above-described invention, various features can be provided as follows.

(Aspect 1)

A disposable diaper for pets, comprising:

a back-side waist area, an abdomen-side waist area and a crotch area between the back-side waist area and the abdomen-side waist area, a flap formed in the abdomen-side waist area and having an end on the back side, a diaper longitudinal direction in which the back-side waist area, the crotch area and the abdomen-side waist area contiguously extend when the disposable diaper is not worn by a pet, and a diaper transverse direction crossing the diaper longitudinal direction, both ends in the diaper longitudinal direction, and both ends in the diaper transverse direction, a diaper longitudinal center line extending in the diaper longitudinal direction and passing through a center of the disposable diaper in the diaper transverse direction, a diaper center point which bisects the diaper longitudinal center line on the disposable diaper, a tail insertion opening formed in a prescribed region in the diaper longitudinal direction, an absorbent core formed on one side of the tail insertion opening in the diaper longitudinal direction and disposed in a prescribed region extending over the crotch area and the abdomen-side waist area, a fastening part having a prescribed length and provided on the flap, a fastening part longitudinal direction in which the length of the fastening part extends and a fastening part transverse direction crossing the fastening part longitudinal direction, a fastening part midpoint which bisects a length of the fastening part in the fastening part transverse direction on a boundary between the fastening part and the flap, a fastening region provided in the back-side waist area and configured to receive the fastening part, and a shortest line point located on the diaper longitudinal center line at a shortest straight-line distance from the fastening part midpoint to the diaper longitudinal center line via the back-side end of the flap, wherein:

when the disposable diaper is put on the pet, the crotch area and the abdomen-side waist area cover a crotch and an abdomen of the pet, while the back-side waist area is closely fitted to a back of the pet, and the fastening part is fastened to the fastening region, the weight of the absorbent core after excretion is received in the longitudinal direction of the fastening part while the disposable diaper is worn by the pet, and the shortest line point is located on an abdomen-side waist area side beyond the diaper center point.

(Aspect 2)

The disposable diaper as defined in aspect 1, wherein a straight-line distance between the shortest line point and a diaper end center point at which the end in the diaper longitudinal direction in the abdomen-side waist area and the diaper longitudinal center line intersect is 170 to 250 mm.

(Aspect 3)

The disposable diaper as defined in aspect 1, wherein a ratio of a straight-line distance between the shortest line point and the diaper end center point at which the end in the diaper longitudinal direction in the abdomen-side waist area and the diaper longitudinal center line intersect, to a straight-line distance between the abdomen-side end and the back-side end on the diaper longitudinal center line is 45.5 to 50.0%.

(Aspect 4)

The disposable diaper as defined in any one of aspects 1 to 3, comprising:

an absorbent-core non-arrangement region in which the absorbent core is not disposed, a first stretchable elastic member disposed in a prescribed region in the diaper longitudinal direction, and an erected section that is formed by the end in the diaper longitudinal direction being erected by contraction of the first stretchable elastic member.

(Aspect 5)

The disposable diaper as defined in aspect 4, wherein the first stretchable elastic member is disposed in a stretched state between the absorbent core and each of the ends in the diaper transverse direction, and forms leg gathers by contracting.

(Aspect 6)

The disposable diaper as defined in aspect 4, comprising a leakproof sheet, wherein the first stretchable elastic member is disposed in a stretched state in the leakproof sheet and forms a leakproof wall and leakproof gathers by contracting.

(Aspect 7)

The disposable diaper as defined in any one of aspects 4 to 6, wherein the erected section is formed on the end in the diaper longitudinal direction in the abdomen-side waist area.

(Aspect 8)

The disposable diaper as defined in any one of aspects 4 to 6, wherein the erected section is formed on the end in the diaper longitudinal direction in the back-side waist area.

(Aspect 9)

The disposable diaper as defined in any one of aspects 4 to 6, wherein the erected section comprises a first erected section formed on the end in the diaper longitudinal direction in the abdomen-side waist area and a second erected section formed on the end in the diaper longitudinal direction in the back-side waist area.

(Aspect 10)

The disposable diaper as defined in any one of aspects 4 to 9, wherein an erection sheet is provided in an end region of the absorbent-core non-arrangement region in the diaper longitudinal direction, and the erection sheet is erected by contraction of the first stretchable elastic member and forms the erected section.

(Aspect 11)

The disposable diaper as defined in aspect 10, wherein the erection sheet is a second stretchable elastic member.

(Aspect 12)

The disposable diaper as defined in any one of aspects 4 to 11, wherein, when the disposable diaper is ready to be put on the pet, the first stretchable elastic member is already contracted so that the erected section is already formed.

(Aspect 13)

The disposable diaper as defined in any one of aspects 4 to 12, wherein, while the disposable diaper is worn by the pet, the first stretchable elastic member is maintained in a contracted state so that the erected section is maintained in an erected state.

(Aspect 14)

The disposable diaper as defined in any one of aspects 1 to 13, comprising the first stretchable elastic member, the second stretchable elastic member, and a contraction force intersecting region in which contraction force of the first stretchable elastic member and contraction force of the second stretchable elastic member intersect with each other.

(Aspect 15)

The disposable diaper as defined in aspect 14, wherein the second stretchable elastic member is disposed between the absorbent core and each of the ends in the diaper transverse direction and forms waist gathers by contracting.
(Aspect 16)
The disposable diaper as defined in aspect 14 or 15, wherein the first stretchable elastic member and the second stretchable elastic member are overlapped with each other.
(Aspect 17)
The disposable diaper as defined in any one of aspects 14 to 16, wherein a first curved part is formed in the ends in the diaper longitudinal direction and curved outward when the disposable diaper is put on the pet, and a second curved part is formed in the contraction force intersecting region and curved inward when the disposable diaper is put on the pet.
(Aspect 18)
The disposable diaper as defined in any one of aspects 14 to 17, wherein the contraction force intersecting region is formed in the abdomen-side waist area.
(Aspect 19)
The disposable diaper as defined in any one of aspects 14 to 17, wherein the contraction force intersecting region is formed in the back-side waist area.
(Aspect 20)
The disposable diaper as defined in any one of aspects 14 to 17, wherein the contraction force intersecting region includes a first contraction force intersecting region formed in the abdomen-side waist area and a second contraction force intersecting region formed in the back-side waist area.
(Aspect 21)
The disposable diaper as defined in any one of aspects 14 to 20, wherein, when the disposable diaper is ready to be put on the pet, the first and second stretchable elastic members are already contracted so that the contraction force intersecting region is already formed.
(Aspect 22)
The disposable diaper as defined in any one of aspects 14 to 21, wherein, while the disposable diaper is worn by the pet, the first and second stretchable elastic members are maintained in a contracted state so that the contraction force intersecting region is maintained.
(Aspect 23)
The disposable diaper as defined in any one of aspects 1 to 22, comprising:
the first stretchable elastic member arranged in the diaper longitudinal direction,
a fixed part for fixing contraction force of the stretchable elastic member onto the absorbent-core non-arrangement region, and
a crotch-side erected section that is formed by the absorbent-core non-arrangement region being erected between the fixed part and the absorbent core by contraction of the stretchable elastic member.
(Aspect 24)
The disposable diaper as defined in aspect 23, wherein the erected section is formed between an end of the absorbent core in the diaper longitudinal direction and the tail insertion opening in the crotch area.
(Aspect 25)
The disposable diaper as defined in aspect 23 or 24, wherein, when the disposable diaper is ready to be put on the pet, the first stretchable elastic member is already contracted so that the crotch-side erected section is already formed.
(Aspect 13)
The disposable diaper as defined in any one of aspects 23 to 25, wherein, while the disposable diaper is worn by the pet, the first stretchable elastic member is maintained in a contracted state so that the crotch-side erected section is maintained in an erected state.

DESCRIPTION OF THE NUMERALS

100, 101, 102, 103, 104, 105, 106, 107, 108, 109, 1000 disposable pet diaper
100A end in the diaper transverse direction
100P diaper center point
100Y1 flap boundary line
100Y2 diaper longitudinal center line
100Z1 inside surface
100Z2 outside surface
110, 1110 abdomen-side waist area
110A, 1110A abdomen-side end
110AP abdomen-side end center point
120, 1120 crotch area
120A leg-side end
130, 1130 back-side waist area
130A, 1130A back-side end
130AP back-side end center point
140A flap
140B body
150, 1150 abdomen-side flap
150A end in the diaper transverse direction
150B, 1150B back-side end
160, 1160 back-side flap
170 absorbent-core non-arrangement region
171 abdomen-side erected region
172 back-side erected region
173 crotch-side erected region
180 contraction force intersecting region
181 first contraction force intersecting region
182 second contraction force intersecting region
183 second curved part
184 second abdomen-side curved part
185 second back-side curved part
190, 1190 tail insertion opening
191 cut
200, 2000 absorbent core
210 abdomen-side end
220 back-side end
230 end in the diaper transverse direction
300, 301, 302, 303, 304, 3000 fastening part
310 free part
320 fixed part
300P1 fastening part midpoint
300P2 shortest line point
300L shortest straight-line distance
300X fastening part longitudinal direction
300Y fastening part transverse direction
400, 401, 401A, 401B, 401C, 402, 402A, 402B, 403, 404, 405, 406, 407, 408, 4000 leg stretchable elastic member
410, 4410 leg gather
420 fourth curved part
500 waist stretchable elastic member
510, 511, 512, 513, 514 abdomen-side waist stretchable elastic member
520 back-side waist stretchable elastic member
530 waist gather
540 first curved part
541 first abdomen-side curved part
542 first back-side curved part
600, 601, 602, 603, 604, 605, 6000 leakproof sheet stretchable elastic member
610 contraction force fixing part
620 abdomen-side contraction force fixing part
630 back-side contraction force fixing part
640 third curved part
700 erected section 710 abdomen-side erected section
720 back-side erected section
730 crotch-side erected section
740 erection sheet
800, 8000 leakproof sheet
810 folded part
820 leakproof wall
830 leakproof sheet fixed part
840 leakproof gather
850 excrement storage space
900, 9000 fastening region
910 liquid-permeable sheet
920 liquid-resistant sheet
930 outer sheet
D1 diaper longitudinal length
D2 measured length
F1 contraction force of the leg stretchable elastic member
F2 contraction force of the waist stretchable elastic member
F3 contraction force acting on the contraction force intersecting region
X diaper transverse direction
Y diaper longitudinal direction
α pet
α1 leg of pet
α2 back of pet
α3 abdomen of pet

The invention claimed is:

1. A disposable diaper for pets, said disposable diaper comprising:
   a back-side waist area, an abdomen-side waist area and a crotch area between the back-side waist area and the abdomen-side waist area,
   a flap formed in the abdomen-side waist area,
   a diaper longitudinal direction in which the back-side waist area, the crotch area, and the abdomen-side waist area contiguously extend when the disposable diaper is not worn on a pet, and a diaper transverse direction crossing the diaper longitudinal direction,
   two longitudinal ends opposing each other in the diaper longitudinal direction, and two lateral ends opposing each other in the diaper transverse direction,
   a diaper longitudinal center line extending in the diaper longitudinal direction and passing through a center of the disposable diaper in the diaper transverse direction,
   a diaper center point which bisects the diaper longitudinal center line on the disposable diaper,
   a tail insertion opening in a prescribed region in the diaper longitudinal direction,
   an absorbent core on one side of the tail insertion opening in the diaper longitudinal direction and extending over the crotch area and the abdomen-side waist area,
   a fastening part having a prescribed length and provided on the flap,
   a fastening part longitudinal direction in which the fastening part is elongated and a fastening part transverse direction crossing the fastening part longitudinal direction,
   a fastening part midpoint which bisects a width of the fastening part in the fastening part transverse direction, the fastening part midpoint being on a boundary between the fastening part and the flap,
   a fastening region provided in the back-side waist area and configured to receive the fastening part,
   an absorbent-core non-arrangement region in which the absorbent core is not disposed,
   a first stretchable elastic member disposed in a stretched state and extending in the diaper longitudinal direction between the absorbent core and each of the two lateral ends,
   a second stretchable elastic member disposed in a stretched state and extending in the diaper transverse direction between the absorbent core and each of the two longitudinal ends, and
   a shortest line point located on the diaper longitudinal center line, the shortest line point, a back-side end of the flap, and the fastening part midpoint defining a shortest straight-line distance from the fastening part midpoint to the diaper longitudinal center line via the back-side end of the flap,
   wherein
   a contraction force of the first stretchable elastic member and a contraction force the second stretchable elastic member intersect with each other in a contraction force intersecting region,
   the shortest line point is located closer to the abdomen-side waist area than to the diaper center point,
   when the disposable diaper is worn on the pet,
      each of the two longitudinal ends has a first curved part that is curved outwardly and adapted to curve away from the pet,
      the contraction force intersection region has a second curved part that is curved inwardly and adapted to curve toward the pet,
      one of the two longitudinal ends is erected by contraction of the first stretchable elastic member to form an erected section,
      the crotch area and the abdomen-side waist area are adapted to cover a crotch and an abdomen of the pet, respectively,
      the back-side waist area is adapted to be fitted to a back of the pet,
      the fastening part is fastened to the fastening region, and
      a weight of the absorbent core after excretion is received in the fastening part longitudinal direction of the fastening part, and
   the first stretchable elastic member and the second stretchable elastic member overlap each other in a diaper thickness direction crossing the diaper longitudinal direction and the diaper transverse direction.

2. The disposable diaper as defined in claim 1, wherein a straight-line distance between the shortest line point and a diaper end center point at which one of the two longitudinal ends in the abdomen-side waist area and the diaper longitudinal center line intersect is 170 to 250 mm.

3. The disposable diaper as defined in claim 1, wherein
   a first straight-line distance is defined between the shortest line point and a diaper end center point at which one of the two longitudinal ends in the abdomen-side waist area and the diaper longitudinal center line intersect,
   a second straight-line distance is defined between the two longitudinal ends on the diaper longitudinal center line, and
   a ratio between the first straight-line distance and the second straight-line distance is 45.5 to 50.0%.

4. The disposable diaper as defined in claim 1, wherein the first stretchable elastic member forms leg gathers by contraction of the first stretchable elastic member.

5. The disposable diaper as defined in claim 1, further comprising a leak proof sheet, wherein the first stretchable elastic member is disposed in the stretched state in the leak proof sheet to form a leak proof wall and leak proof gathers by contraction of the first stretchable elastic member.

6. The disposable diaper as defined in claim 1, wherein the erected section is formed on one of the two longitudinal ends in the abdomen-side waist area.

7. The disposable diaper as defined in claim 1, wherein, when the disposable diaper is ready to be worn on the pet, the first stretchable elastic member is already contracted to already form the erected section.

8. The disposable diaper as defined in claim 1, wherein, while the disposable diaper is worn on the pet, the first stretchable elastic member maintains a contracted state to maintain the erected section in an erected state.

9. The disposable diaper as defined in claim 1, wherein the contraction force intersecting region is in the abdomen-side waist area.

10. The disposable diaper as defined in claim 1, wherein, when the disposable diaper is ready to be worn on the pet, the first and second stretchable elastic members are already contracted to already form the contraction force intersecting region.

11. The disposable diaper as defined in claim 1, wherein, while the disposable diaper is worn on the pet, the first and second stretchable elastic members maintain a contracted state to maintain the contraction force intersecting region.

12. The disposable diaper as defined in claim 1, wherein the second stretchable elastic member forms waist gathers by contraction of the second stretchable elastic member.

13. The disposable diaper as defined in claim 1, further comprising:
    a fixed part configured to fix the first stretchable elastic member onto the absorbent-core non-arrangement region, and
    the absorbent-core non-arrangement region between the fixed part and the absorbent core is erected by contraction of the first stretchable elastic member to form a crotch-side erected section.

14. The disposable diaper as defined in claim 13, wherein the crotch-side erected section is formed between an end of the absorbent core in the diaper longitudinal direction and the tail insertion opening in the crotch area.

15. The disposable diaper as defined in claim 13, wherein, when the disposable diaper is ready to be worn on the pet, the first stretchable elastic member is already contracted to already form the crotch-side erected section.

16. The disposable diaper as defined in claim 13, wherein, while the disposable diaper is worn on the pet, the first stretchable elastic member maintains a contracted state to maintain the crotch-side erected section in an erected state.

17. The disposable diaper as defined in claim 1, wherein the first stretchable elastic member continuously extends in the longitudinal direction between the two longitudinal ends.

* * * * *